United States Patent
Shimada et al.

(10) Patent No.: US 9,228,107 B2
(45) Date of Patent: Jan. 5, 2016

(54) (METH)ALLYLSILANE COMPOUND, SILANE COUPLING AGENT THEREOF, AND FUNCTIONAL MATERIAL USING THE SAME

(75) Inventors: Toyoshi Shimada, Souraku-gun (JP); Yoshinori Takamatsu, Nara (JP)

(73) Assignees: KYOEISHA CHEMICAL CO., LTD., Osaka (JP); TOYOSHI SHIMADA, Kyoto (JP)

( * ) Notice: Subject to any disclaimer, the term of this patent is extended or adjusted under 35 U.S.C. 154(b) by 0 days.

(21) Appl. No.: 14/129,824

(22) PCT Filed: Jun. 28, 2012

(86) PCT No.: PCT/JP2012/066600
§ 371 (c)(1),
(2), (4) Date: Jan. 31, 2014

(87) PCT Pub. No.: WO2013/002347
PCT Pub. Date: Jan. 3, 2013

(65) Prior Publication Data
US 2014/0200311 A1 Jul. 17, 2014

(30) Foreign Application Priority Data

Jun. 29, 2011 (JP) .................. 2011-144727
Jun. 29, 2011 (JP) .................. 2011-144728
Aug. 9, 2011 (JP) .................. 2011-173899

(51) Int. Cl.
C09D 143/04 (2006.01)
C07F 7/08 (2006.01)
C07F 7/18 (2006.01)
C08F 230/08 (2006.01)

(52) U.S. Cl.
CPC .............. *C09D 143/04* (2013.01); *C07F 7/081* (2013.01); *C07F 7/082* (2013.01); *C07F 7/0803* (2013.01); *C07F 7/0809* (2013.01); *C07F 7/0818* (2013.01); *C07F 7/0836* (2013.01); *C07F 7/0847* (2013.01); *C07F 7/0874* (2013.01); *C07F 7/1844* (2013.01); *C07F 7/1852* (2013.01); *C08F 230/08* (2013.01)

(58) Field of Classification Search
CPC ....... C07F 7/082; C07F 7/0847; C07F 7/1852
See application file for complete search history.

(56) References Cited

U.S. PATENT DOCUMENTS

| | | | |
|---|---|---|---|
| 5,667,674 | A | 9/1997 | Hanggi et al. |
| 5,876,595 | A | 3/1999 | Hanggi et al. |
| 5,968,652 | A | 10/1999 | Hanggi et al. |
| 2004/0067436 | A1 | 4/2004 | Kinsho et al. |
| 2008/0227939 | A1 | 9/2008 | Mizoshita et al. |
| 2008/0227941 | A1 | 9/2008 | Mizoshita et al. |
| 2009/0270590 | A1 | 10/2009 | Jun et al. |
| 2013/0060014 | A1 | 3/2013 | Jun et al. |

FOREIGN PATENT DOCUMENTS

| | | |
|---|---|---|
| JP | A-2000-502952 | 3/2000 |
| JP | A-2004-175793 | 6/2004 |
| JP | A-2004-238487 | 8/2004 |
| JP | A-2006-089588 | 4/2006 |
| JP | A-2008-214314 | 9/2008 |
| JP | A-2008-247886 | 10/2008 |
| JP | A-2009-502713 | 1/2009 |
| JP | A-2009-138097 | 6/2009 |
| JP | A-2010-090302 | 4/2010 |
| WO | 97/25140 A1 | 7/1997 |
| WO | WO 97/25140 * | 7/1997 |
| WO | 2007/024055 A1 | 3/2007 |
| WO | WO 2010/057080 A1 | 5/2010 |

OTHER PUBLICATIONS

Database CA [Online] Chemical Abstracts Service, XP-002734051, (1997), Klos et al., Aβ-Hydroxyethyl Carbanion Equivalent.
Boysen, et al., "Synthesis of Selectively Functionalized Carbosilane Dendrimers with a Carbohydrate Core," Organic Letters, vol. 1, No. 12, (1999), p. 1925-1927.
Chang, et al., "Amphiphilic Linear PEO—Dendritic Carbosilane Block Copolymers," Macromolecules (2000), 33, p. 4496-4500.
de Raadt, et al., "A one-step C-linked disaccharide synthesis from carbohydrate allylsilanes and tri-O-acetyl-D glucal," Carbohydrate Research, 220 (1991), p. 101-115.
Landais, et al., "A New Synthesis and Stereocontrolled Functionalization of Substituted Silacyclopent-3-enes," J. Org. Chem., (2003), 68, p. 2779-2789.
Jan. 19, 2015 extended European Search Report issued in European Application No. 12804224.9.

(Continued)

*Primary Examiner* — Robert Harlan
(74) *Attorney, Agent, or Firm* — Oliff PLC

(57) ABSTRACT

A (meth)allylsilane compound that a functional group of a (meth)allylsilyl group or a halogenosilyl group bonded to the (meth)allylsilyl group via a spacer group is bonded directly or through a divergent spacer group to a dehydrogenated residue of an amino group of an amino group-containing compound; a carbaminic acid ester group or an amide group derived from a dehydrogenated residue of the amino group; an aromatic compound; a polymerizable unsaturated groups; perfluoro group; a dehydrogenated residue of saccharide or a carbohydrate polyol (excluding when the divergent spacer group is an alkylene group, or an alkylene group and an arylene group); a dehydrogenated residue of an amino acid; a halogenosilyl group; or a substituted silyl group in which a halogen of the halogenosilyl group is substituted.

42 Claims, No Drawings

(56) References Cited

OTHER PUBLICATIONS

Sep. 18, 2012 International Search Report issued in International Application No. PCT/JP2012/066600.

Maegawa et al., "Preparation of functionalized aryl(diallyl)ethoxysilanes and their palladium-catalyzed coupling reactions giving sol-gel precursors," *Tetrahedron*, 2007, pp. 11467-11474, vol. 63, Elsevier Ltd.

Abel et al., "The Reaction of Perhalogenoketones with Allylic Derivatives of Silicon and Tin," *Journal of Organometallic Chemistry*, 1975, pp. 199-229, vol. 84, Elsevier Sequoia S.A., Lausanne, The Netherlands.

May 6, 2015 Office Action issued in Chinese Patent Application No. 201280032441.9.

Klos et al., "A b-Hydroxyethyl Carbanion Equivalent," J. Org. Chem., vol. 62, No. 11, 1997, pp. 3758-3761.

* cited by examiner

(METH)ALLYLSILANE COMPOUND, SILANE COUPLING AGENT THEREOF, AND FUNCTIONAL MATERIAL USING THE SAME

TECHNICAL FIELD

The present invention relates to a (meth)allylsilane compound, a silane coupling agent thereof, and a functional material using the same. The (meth)allylsilane compound is used for developing functions, for example, optical properties such as anti-reflective and anti-cloudiness (or anti-fogging) properties, separation characteristics in column chromatography, charge transport properties of electronic materials, catalytic properties for chemical reaction, surface protection and lipophilic properties, abrasion resistance or oil repellency, water repellency or functions such as anti-scratch resistance. The (meth)allylsilane compound is included in a coating composition and a reactive functional group that can be chemically bonded to a substrate in the composition or the surface of a base material so that it can be coated on the base material and reacted there through silane coupling reactions to introduce or realize the functions.

BACKGROUND ART

Organic/inorganic hybrid materials such as organic siloxane compounds exhibit both characteristics of organic properties such as hydrophobicity derived from the organic group and inorganic properties such as hydrophilicity or high reactivity to water and condensational reactivity derived from a siloxy group. A functional material having various functions such as a refractive index control function, a light absorption function, a light emitting function, a charge transport function, etc. can be prepared through polymerization under sol-gel reaction conditions from such organic/inorganic hybrid materials such as especially the organic siloxanes containing a trialkoxysilyl group.

However, the organic/inorganic hybrid materials may not perform a desired silane coupling reaction with other functional groups due to the fact that tri-alkoxy silyl groups thereof tend to preferentially perform exchange reactions with alkoxy groups or silanol groups of other molecules or may be hard to perform sol-gel reactions due to the fact that tri-alkoxy silyl groups tend to perform hydrolysis reactions, when compared to polymerization reaction in which chemical products or reagents which contain no siloxane group are performed through condensation or polymerization. Furthermore the organic/inorganic hybrid materials is difficult to be purified by silica-gel chromatography and also difficult to be stocked for a long period of time, due to the fact that the hybrid materials being unstable to moisture and water. Accordingly, functional materials prepared from the conventional organic/inorganic hybrid materials are poor in yield, in production efficiency and purity.

In Non Patent Document 1, the inventors of the present invention disclose preparation of functional aryl (diallyl) ethoxy silanes which could be precursors in sol-gel reaction and disclose their palladium-catalyzed coupling reaction. Further, in Patent Document 1, the inventors of the present invention disclose a method for preparing an organic silica composite material such as a mesoporous body, etc. through hydrolysis and polycondensation reactions of an organic silane compound having allyl groups in a solvent.

Compounds containing a perfluoro group have a strong bond between a carbon atom and a fluorine atom, so that it has an excellent heat resistance and has further small coefficient of friction or low refraction index, due to the existence of fluorine atoms. Therefore, such compound containing the perfluoro group is used to give water- or oil-repellency, to exhibit a moderate lipophilicity, anti-reflective property and also to protect the surface of a substrate by forming a coating onto a surface of a base material or applying paint thereof. For example, in Patent Document 2, optical members that are made of a hardened material prepared from fluorine-substituted-alicyclic group-containing (meth)acrylic acid ester through heating or an active energy ray irradiation, are disclosed. In Patent Document 3, fine particles which are cross-linked with each other and are made of fluorine containing acrylic polymer which is modified by a crosslinkable functional group and hardened by the crosslinkable functional group, and an optical material containing the bonded fine particles are disclosed. In Patent Documents 2 and 3, a fluorine containing polymer is not chemically bonded directly to the various base materials such as silica particles, glass plates, metal plates, resin films, etc. Fluorine-containing polymers have poor scratch resistance and are easily scratched when contacted.

An organic silane compound which can be a silane coupling agent developing various functionalities has long been desired. Such organic silane compound has more reactivity than the conventional organic/inorganic hybrid materials; has reaction-specific, charge-specific, or stereo-specific property; can be induced from various starting compounds such as amino group-containing compounds; has moderate hydrophilic and hydrophobic properties and three-dimensional characteristics; and further has a moderate condensational or polycondensational reactivity to give functions to various raw materials. Further, a fluorine-containing organic silane compound, which can develop much better scratch resistance, can form a stronger bonding derived from a direct chemical bonding, and can develop moderate water repellency and oil repellency, has been desired. The layer of the fluorine-containing organic silane compound can be more excellent rather than a merely formed coating layer which is attached physically, through roughness of the surface and electrostatic attraction, to the surface of the base material such as particles, plates or film-like ones.

PRIOR ART DOCUMENT

Non-Patent Document

[Non-Patent Document 1] Yoshifumi Maegawa, *Tetrahedron*, 2007, vol. 63, p. 11467-11474

Patent Document

[Patent Document 1] Japan Patent Publication: JP2006-89588A1

[Patent Document 2] Japan Patent Publication: JP2004-238487A1

[Patent Document 3] Japan Patent Publication: JP2010-90302A1

DISCLOSURE OF THE INVENTION

Problem to be Solved by the Invention

The present invention was made to solve the problems. An object of the present invention is to provide a (meth)allylsilane compound as a raw material which is used for developing functionality of the optical properties such as anti-reflective and anti-fogging properties, separation characteristics in column chromatography, charge transport properties of electronic materials, catalytic properties of chemical reactions, lipophilic or oil repellency and water repellency, surface protective properties, and scratch resistance, on a base material. Thus (meth)allylsilane compound is an organosilane compound which is preferably bonded chemically to the free amines, amino acids, and various raw compounds such as amino group-containing compounds illustrated by an ester, an amide or a salt etc. thereof and can be prepared and purified easily and is stable and easy to handle. An object of the present invention is to provide a perfluoroalkyl group-containing (meth)allylsilane compound which can develop a moderate lipophilic or oil repellency and a moderate water repellency to the base material by exposure of fluorine atoms of the perfluoro group in the molecule after forming a directly tightly chemically bond to the various base materials having arbitrary shape made of various raw material such as silica particles, glass plates, metal plates, resin film, etc., or can develop functionalities such as anti-scratch property as well as antifouling property, anti-scratch property onto a layer made from a composition through binding substrates such as fillers contained in the composition to be coated on the base materials. The perfluoroalkyl group-containing (meth)allylsilane compound has a simple structure and is productionized.

Other object of the present invention is to provide a functional material which can develop those functionalities while holding silyl-containing groups on a surface of the base material in high density simply through silane coupling to the base material using the (meth)allylsilane compound as the silane coupling agent. Further other object is to provide a coating composition which is used for coating the base materials with such (meth)allylsilane compound and a coating material by attaching the coating composition to the base materials.

Means for Solving the Problems

The present invention is a (meth)allylsilane compound: that a functional group selected from a reactive functional group comprising of a (meth)allylsilyl group that may have a substituent; or a reactive functional group comprising of a halogenosilyl group bonded to the (meth)allylsilyl group via a spacer group containing an alkylene group, an arylene group, an aralkylene group and/or a silyl group,
is bonded directly or through a divergent spacer group which contains at least any one selected from the group consisting of an alkylene group, an arylene group, an aralkylene group, a silyl group, an oxy group, an alkylene ether group and a poly(alkyleneoxy) group,
to at least any one of group selected from the group consisting of a dehydrogenated residue of an amino group of an amino group-containing compound; a carbaminic acid ester group or an amide group derived from a dehydrogenated residue of the amino group; an aromatic compound selected from a biphenyl compound, a triallylamine compound and a carbazole compound; a polymerizable unsaturated groups; any one of perfluoro group selected from the group consisting of a perfluoro alkyl group, a perfluoroalkenyl group and a perfluoroaralkyl group; a dehydrogenated residue of saccharide or a carbohydrate polyol (excluding when the divergent spacer group is an alkylene group, or an alkylene group and an arylene group); a dehydrogenated residue of an amino acid; a halogenosilyl group; or a substituted silyl group in which a halogen of the halogenosilyl group is substituted with an alkyl group, an aryl group, a hydroxyl group, an alkoxy group, an aryloxy group, a mercapto group, an alkylthio group, an arylthio group, an amino group, a dehydrogenated residue of the sugar, a dehydrogenated residue of a hydrocarbon-based polyol, a dehydrogenated residue of an amino acid, a phosphoryl group, a silyl group or a silyloxy group.

In the (meth)allylsilane compound, the (meth)allylsilyl group is a mono-, di- or tri-(meth)allylsilyl group.

In the (meth)allylsilane compound, the (meth)allylsilyl group is selected from the group consisting of an alkyl[di(meth)allylsilyl group and a dialkyl[(meth)allyl]silyl group each of which has a linear, branched and/or cyclic carbon chain having a carbon number of 1 to 24, and a tri(meth)allylsilyl group.

In the (meth)allylsylane compound, the silyl of at least any one selected from the group consisting of the (meth)allylsilyl group, the silyl group, the halogenosilyl group and the substituted silyl group is mono- or di-substituted with a linear, branched and/or cyclic alkyl group having a carbon number of 1 to 24.

In the (meth)allylsilane compound, the amino group-containing compound is primary amines, secondary amines, or amino acids.

In the (meth)allylsilane compound, the halogenosilyl group is a fluoro-, chloro-, bromo- or iodo-silyl group.

In the (meth)allylsilane compound, the polymerizable unsaturated group is an acrylic group, methacrylic group, styril group or terminally unsaturated alkenyl group.

In the (meth)allylsilane compound, the perfluoro group is a linear, branched or cyclic carbon chain having a carbon number of 1 to 24.

In the (meth)allylsilane compound, the perfluoro group is any one of the perfluoroalkyl group selected from a perfluoroalkenyl group having a carbon number of 1 to 24 and a perfluorocycloalkyl group having a carbon number of 3 to 24; the perfluoroalkenyl group selected from a perfluoroalkenyl group having carbon number is 2 to 24 and a perfluorocycloalkenyl group having carbon number is 3 to 24; and the perfluoroaralkyl group having the carbon number of 7 to 24.

In the (meth)allylsilane compound, the perfluoro group is the perfluoroalkenyl group represented by n-$C_6F_{13}$— group or represented by the following chemical formula (I).

(I)

In the spacer group of the (meth)allylsilane compound, an alkylene group, an arylene group, an aralkylene group and an alkylene ether group are a linear and/or branched chain having a carbon number of 1 to 36, and poly(alkyleneoxy) group has its molecular weight of 88 to 50,000.

In the (meth)allylsilane compound, a hydroxyl group, a (meth)acryloyl group and/or a (meth)acryloyloxy group is bonded to the divergent spacer group.

In the (meth)allylsilane compound, a (meta)silyl is carbon-increased to an allyl of the (meth)allylsilyl.

In the (meth)allylsilane compound, the (meth)allylsilyl group is formed into a dendrimer-like structure.

In the (meth)allylsilane compound, the (meth)allylsilyl group is formed by bonding an unsubstituted alkyl onto a silane atom thereof.

A method for manufacturing a (meth)allylsilane compound having a perfluoro group comprises:

a chemical reaction process for reacting any one of a perfluoroalkyl-1,2-epoxypropane having a linear, branched and/or cyclic perfluoroalkyl of carbon number of 1 to 24, a hexafluoropropene trimer, and a substituent which a glycidol or a glycerin diglycidylether is substituted with a hexafluoropropene trimer, to any one of organic metal compounds which may have a substituent and are selected from a tri-(meth)allylsilyl alkylene metal compound having a linear, branched and/or cyclic alkylene of a carbon number 1 to 36, and a alkyl[di(meth)allyl]silyl alkylene metal compound and dialkyl[(meth)allyl]silyl alkylene metal compound having a linear, branched and/or cyclic alkyl of a carbon number 1 to 24 and a linear, branched and/or cyclic alkylene of a carbon number 1 to 36, to manufacture the (meth)allylsilane compound having the perfluoro group.

As regards the method for manufacturing the (meth)allylsilane compound having the perfluoro group, after the chemical reaction process between the organic metal compound and either one of the substituent and the perfluoroalkyl-1,2-epoxypropane is reacted, a hydroxyl group generated here is esterified with a (meth)acrylic ester group.

A silane coupling agent comprises the (meth)allylsilane compound.

In the silane coupling agent, the (meth)allylsilane compound has a functional group selected from the group consisting of a catalytic functional group, a conjugated functional group and a molecular recognition functional group.

In the silane coupling agent, the catalytic functional group is a phosphine-containing functional group and/or a heterocycle-containing functional group; the conjugated functional group is a carbazole ring-containing functional group, a polyene-containing functional group, a polyyne-containing functional group, and/or a polyarene-containing functional group; and the molecular recognition functional group is an optically active site-containing functional group.

A method for manufacturing a silane coupling agent comprises:

a process for reacting a (meth)allylsilane compound having a polymerizable unsaturated group that has two reactive functional groups of (meth)allylsilyl group and a halogenosilyl group which are bonded via a spacer group containing an alkyl group, aryl group, aralkyl group and/or silyl group thereto, or has the two reactive functional groups bonded directly or via a divergent spacer group containing alkyl group, aryl group, aralkyl group and/or oxy group to the two reactive functional groups or any one of the two reactive functional groups, to occur a chemical reaction at the (meth)allylsilane compound so that a halogen of the halogeno silyl group is substituted with an alkyl group, an aryl group, a hydroxyl group, an alkoxy group, an allyloxy group, a mercapto group, an alkylthio group, an arylthio group, an amino group, a dehydrogenated residue of sugar, a dehydrogenated residue of a hydrocarbon-based polyol, a hydrogenated residue of an amino acid, a phosphoryl group, a silyl group, or a silyloxy group.

In a functional material, on a base material on which a surface hydroxyl group is exposed, the silane coupling agent is ether-bonded by silane-coupling via the surface hydroxy group.

In the functional material, another silane coupling agent having an alkyl group, a partial fluoroalkyl group, a perfluoroalkyl group and/or an aryl group, each of which may have a substituent, and having a trialkoxysilyl group, a dialkoxy allyl silyl group, an alkoxy diallyl silyl group or a triallyl silyl group is further ether-bonded on the base material via the surface hydroxyl group through silane coupling.

In the functional material, a functional group in the (meth)allylsilane compound is exposed and is derived at least from any one selected from the group consisting of a dehydrogenated residue of the amino group of the amino group-containing composition; a carbamate ester group or an amide group derived from a dehydrogenated residue of the amino group; a polymerizable unsaturated group; at least any one of perfluoro group selected from the group consisting of the perfluoroalkyl group, the perfluoroalkenyl group, and the perfluoroaralkyl group; a dehydrogenated residue of the sugar or the carbon hydrogen-based polyol; a dehydrogenated group of the amino acid; the halogenosilyl group; a substituted silyl group in which a halogen of the halogenosilyl group is substituted with an alkyl group, an aryl group, a hydroxyl group, an alkoxy group, an allyloxy group, a mercapto group, an alkylthio group, an allylthio group, an amino group, a dehydrogenated residue of sugar, a dehydrogenated residue of a carbon hydrogen-based polyol, a dehydrogenated residue of an amino acid, a phosphorile group, a silyl group or a silyloxy group.

In the functional material, the base material is a glass base material, a metal base material, a ceramics base material, a resin base material or a surface coating base material made of any one of the base materials, each of which are treated with the silane coupling agent.

The functional material is an anti-fogging material, an optical material, a column chromatography carrier, a catalyst, or an electronic material, each of which are prepared by surface modification treated with the silane coupling agent.

In the functional material, the base material is a glass particle, a silica gel particle, an alumina particle, a metal particle, a ceramic particle, a resin particle or the particles having a chemically modified surface made of any one of the base materials, and the functional material is used as the column chromatography carrier for eluting and/or separating a solute through hydrophilicity, hydrophobicity, adsorptive property and/or stereospecificity of the silane coupling agent.

In the functional material, the base material is a glass base material, a metal base material, a ceramics base material, a resin base material or a surface-coated base material made of any one of the base materials, and the functional material is the catalyst exhibiting a catalyzing function induced from the silane coupling agent.

In the functional material, the base material is a glass base material, a metal base material, a ceramics base material, a resin base material of surface modified base material made of any one of the base materials, and the functional material is the electronic material surface-treated with the silane coupling agent.

In the functional material, the ether bond is formed by the silane coupling of the silane coupling agent through a sol-gel method.

In the functional material, the ether bond is formed in anhydrous organic solvent by the silane coupling of the silane coupling agent.

In the functional material, the ether bond is formed by the silane coupling of the silane coupling agent at least in the presence of a hydrochloric acid, a sulfuric acid, a tetraalkoxysilane, a polycarboxylic acid halide, and a polycarboxylic acid anhydride.

A method for manufacturing a functional material ether-bonded via the surface hydroxyl group comprises:

a step in which silane coupling agent is silane coupling-reacted with the surface hydroxyl group which is exposed on the surface of the substrate.

In the method for manufacturing the functional material, the ether bond is formed by the silane coupling reaction of the silane coupling agent through a sol-gel method.

In the method for manufacturing the functional material, another silane coupling agent having an alkyl group, a partial fluoroalkyl group, a perfluoroalkyl group and/or an aryl group, each of which may have a substituent, and having a trialkoxysilyl group, a dialkoxy allyl silyl group, an alkoxy diallyl silyl group or a triallyl silyl group is further etherbonded on the base material via the surface hydroxyl group through silane coupling reaction.

As regards the method for manufacturing the functional material, after the process of the silane coupling reaction, a trihalogenosilane is reacted with a terminal unsaturated carbon of a (meth)allylsilyl group derived from the silane coupling agent, introducing trihalogenosilyl group; and a (meth)allylsilyl group-containing organic metal compound is reacted with the halogeno group, amplifying the (meth)allylsilyl group-containing group.

As regards the method for manufacturing the functional material, after a process in which the silane coupling agent is treated with an acid aqueous solution, the silane coupling reaction is carried out.

As regards the method for manufacturing the functional material, after a process in which the silane coupling agent is treated with the acid aqueous solution, a process in which the silane coupling agent is reacted with tetraalkoxysilane and a process in which a reaction is performed in the presence of a concentrated sulfuric acid are carried out, then the silane coupling reaction is carried out.

As regards the method for manufacturing the functional material, after a process in which the silane coupling agent is reacted with a polycarboxylic acid halide or polycarboxylic acid anhydride, the silane coupling reaction is carried out.

In the method for manufacturing the functional material, a process to treat with the polycarboxylic acid halide or the polycarboxylic anhydride is performed in an anhydrous organic solvent.

A coating composition comprises the (meth)allylsilane compound.

In the coating composition, the coating composition contains any filler particles selected from the group consisting of a glass particle, a silica particle, an alumina particle, a metal particle, a ceramics particle, a resin particle, and a chemically surface-modified particle made of any one of the particles, and the (meth)allylsilane compound is bonded to a functional group on a surface of the particle thereby.

As regards a coating material, the coating composition is coated on a base material and cured to be a coated layer by heating or irradiation with an active energy ray.

Effect of the Invention

The (meth)allylsilane compound of the present invention is a raw material used for coating a base material and inducing a silane coupling reaction there to develop functionalities, for example, optical properties such as anti-reflective or anti-fogging properties, separation characteristics in a column chromatography, charge transport properties of electronic materials, catalytic properties in chemical reactions, water repellency and oil repellency or lipophilic properties, surface protection, abrasion resistance, etc.

This (meth)allylsilane compound is strongly bonded to a raw (or starting) compound such as various amino group-containing compounds, particularly primary amines, secondary amines, amino acids, more particularly stereospecific amino acids or sugar etc., which can have hydrophilic functional groups such as carboxyl groups that easily result in hydrophilicity. Therefore, it can be prepared in high purity, efficiently and conveniently and it can also be stable to water, moisture and solvent and it can be easy to handle. It does not decompose even when purified under the normal pressure or reduced pressure distillation and in silica gel chromatography, and that it can be stored stably for a long period of time.

When the (meth)allylsilane compound is a perfluoro group-containing (meth)allylsilane compound, and when this compound is applied on a surface of a base material to be protected, the compound reacts through silane-coupling with functional groups on the surface of the base material to give the water and oil repellency or lipophilic properties on the surface. When the compound is bonded to filler as a substrate, which is contained in a composition that is coated on a surface of a base material to be protected, the coated layer of the composition gives scratch resistance to the coated layer. The compound can be a raw material therefor. The perfluoro group containing (meth)allylsilane compound reacts through silane-coupling with a functional group on the surface of the base material, particularly a functional group such as a hydroxyl group generated by surface treatment or originally existed on the surface of the base material, to be bond directly and strongly chemically to the functional group, so that fluorine atoms of the perfluoro group in a molecule can be exposed on the base material. When this perfluoro group-containing (meth)allylsilane compound is bonded to a functional group of the surface of the base material, moderate oil- and water-repellency, an excellent scratch resistance can be developed to the coating materials by exposing the fluorine atoms of the perfluoro group to the air at around the surface of the base material.

As described above, these (meth)allylsilane compound induces moderate hydrophilicity or hydrophobicity, moderate stereospecificity, moderate delocalized electron density, therefore, functionality such as optical properties of anti-fogging and anti-reflection properties, etc., separation properties, charge transport properties, catalytic properties, oil repellency and lipophilic and water repellency, surface protection properties, scratch resistance can be developed on various base materials.

Such (meth)allylsilane compound can be applied on various materials having arbitrary shapes illustrated by planar shapes such as a plate-like shape of glass plates or metal plates etc., and a sheet-like shape or film-like shape of resin films, etc., tridimensional shapes such as a column-like shape and a solid-like shape etc., particle shapes such as a powder-like shape or a grain-like shape of silica particles and the like. Particularly, the (meth)allylsilane compound can chemically bond to the functional group on the surface of inorganic base materials or organic base materials such as silica base materials, glass base materials, metal base materials, ceramic base materials arbitrarily to develop those various functionalities.

For this purpose, this (meth)allylsilane compound can be used as an efficient component of silane coupling agent, and can react through silane coupling by the (meth)allylsilyl group or halogenosilyl group with the reactive functional group on the surface of the material, especially a hydroxyl group generated by the surface treatment or already originally existed on the surface of the base material.

When this silane coupling agent is used, many siloxy groups thereof are involved in coupling. The siloxy groups are derived from a singular or multiple silanol groups that are generated by hydrolysis of (meth)allylsilyl group supported by the base material, are generated by hydrolysis of a singular or multiple (meth)allylsilyl groups in the introduced (meth)allylsilane compound, or are induced from halogenosilyl group in the (meth)allylsilane compound. The siloxy groups are generated on the base material, via the reactive functional group of the base material, and/or via a divergent silanol group of those, in an overlapping manner. As a result, through a simple operation such as a sol-gel method, silyl group-containing groups are easily supported in high density on the surfaces of the base material.

When this silane coupling agent is used, the functional material which can be used in various fields can be produced easily. Since the silane coupling agent has moderate hydrophilic or hydrophobic property, moderate stereospecificity, moderate dislocation of electron density due to the structure of the (meth)allylsilane thereof, accordingly, functionalities such as optical property, separate property, charge transferring property, catalyst property, etc. are developed on these base materials. This functional material can be used for windows, glasses, displays, etc. which abhor cloudiness of surfaces, used for livingware, electronic and electrical appliances which require anti-reflective materials and anti-fogging materials, used for column carriers in column chromatography which require precise and reliable separation, used for charge transport materials of the electrophotographic photoreceptors, used for hole transport materials such as organic electroluminescence devices, used for catalysts for organic synthesis, especially for chiral catalysts which can be used repeatedly, or used for improving surface protective properties in improvement of water or oil repellency, lipophilic property, scratch resistance, etc.

In a method for manufacturing the functional materials, the functional materials, which develops the desired sufficient functionalities, can be produced easily in high quality and high yield production at a lab scale and a plant scale as well.

Furthermore, a coating composition containing the (meth) allylsilane compound is directly applied on various base materials such as silica particles, glass plates, metal plates or resin films, so that the (meth)allylsilane compound can be bonded to functional groups on the surface of the base material. Further, the (meth)allylsilane compound is bonded to functional groups on the surfaces of particles of any one of glass particles, silica particles, alumina particles, metal particles, ceramics particles, resin particles, chemically modified particles thereof, etc. The chemically modified particles and coating resins such as binders, etc. are made into a coating composition and then the coating composition is applied on base materials such as glass plates, metal plates, resin films, etc. thus the coated layer can be formed.

When the coating material is made from a coating composition and the (meth)allyl silane compound is a perfluoro group-containing (meth)allylsilane compound, fluorine atoms derived from the perfluoro groups are exposed to the air, therefore, the coated compound has a little interaction with water, oil, chemical ingredients or foreign materials, showing a moderate water repellency, oil repellency, antifouling properties. The coated compound strongly and stably adhered to the base materials so that the coated compound stably protects the base materials from water, oil, chemical ingredients, foreign materials, etc. for a long period of time. Further, the base material has an excellent anti-scratch property so that the base material is not damaged and is kept clean for a long period of time. Therefore, there is no need to exchange the coating material with time and also no need of reapplication of the coating material for regeneration of coated compound of the layer.

PREFERRED EMBODIMENTS FOR CARRYING OUT THE INVENTION

Preferred embodiments of the present invention will be precisely described below, but the scope of the present invention should not be limited to these embodiments.

The present invention is a (meth)allylsilane compound: that reactive functional groups that may have substituents, which are formed from (meth)allylsilyl groups or formed from halogeno silyl groups, or reactive functional group which are formed from halogenosilyl group bonded to the (meth)allylsilyl group via a spacer group, are bonded directly or through a divergent spacer group, to at least any one of groups selected from the group consisting of dehydrogenated residues of amino groups of amino group-containing compounds; carbaminic acid ester groups or amid groups derived from dehydrogenated residues of amino groups; aromatic compounds; polymerizable unsaturated groups; perfluoro groups; dehydrogenated residues of saccharide (or sugar) or carbohydrate polyols (excluding when the divergent spacer group is an alkylene group, or an alkylene group and an arylene group); dehydrogenated residues of amino acids; halogenosilyl groups; and substituted silyl groups wherein the halogen of the halogenosilyl is substituted with alkyl groups, aryl groups, hydroxyl groups, alkoxy groups, aryloxy groups, mercapto groups, alkylthio groups, arylthio groups, amino groups, dehydrogenated residues of saccharides, dehydrogenated residues of hydrocarbon-based polyols, dehydrogenated residues of amino acids, phosphoryl groups, silyl groups, silyloxy groups.

First preferred embodiment of the present invention is as follows.

The (meth)allylsilane compound of the present invention has at least two substituents selected from the group consisting of a (meth)allylsilyl group that may have a substituent, a halogenosilyl group and a polymerizable unsaturated group. This (meth)allyl may have a substituent if it has an allyl carbon skeleton. Such (meth)allyl means an allyl group ($CH_2$=CH—$CH_2$—) or a methacryl group ($CH_2$=C($CH_3$—$CH_2$—).

One illustrative embodiment of such (meth)allylsilane compound has, for example, a (meth)allylsilyl group or a reactive functional group such as mono-, di- or tri-(meth) allylsilyl group and a halogenosilyl group or another reactive functional group such as fluoro-, chloro-, bromo- or iodo-silyl group, the halogenosilyl group being bonded to the (meth) allylsilyl group via a spacer group containing an alkyl group, an aryl group, an aralkyl group and/or a silyl group.

Another illustrative embodiment of a (meth)allylsilane compound has at least any one of a reactive functional group of a (meth)allylsilyl group such as a mono-, di- or tri-(meth) allylsilyl group and a halogenosilyl group such as a fluoro-, chloro-, bromo- or iodo-silyl group which is bonded to the (meth)allylsilyl group via a spacer group containing an alkyl group, aryl group, aralkyl group and/or silyl group; and further has a polymerizable unsaturated group which is bonded to the reactive functional group directly or via a divergent spacer group containing an alkyl group, aryl group, aralkyl group and/or oxy group.

The (meth)allylsilyl group and the halogeno silyl group, which are reactive functional groups, chemically react with the active functional group such as a hydroxyl group on the surface of the base material to form a covalent bond. Further, the halogensilyl group, which is a reactive functional group, can further react with water, alcohols, silanols, thiols, amines, acids, amino acids, etc.

The polymerizable unsaturated group is an unsaturated group capable of polymerization, through a cation polymerization, an anion polymerization, a radical polymerization, etc. For example, an acrylic group, a methacrylic group, a styryl group which may have a substituent group can be exemplified.

In a spacer group of the (meth)allylsilane compound, as an alkyl group, an alkyl group having 1 to 18, preferably 3 to 6 carbon atoms which is linear, branched or cyclic and saturated or unsaturated alkyl group is exemplified. As an aralkyl group, an arylalkyl group having 7 to 8 carbon atoms such as benzyl group or a phenethyl and the like is exemplified. As an aryl group, aromatic hydrocarbon ring having 6 to 16 carbon atoms such as a phenyl group or heteroaromatic ring such as bipyridine are exemplified. As a silyl group, a tri(meth)allylsilyl group substituted alkyl group, a tri(meth)allylsilyl group substituted aralkyl group, a tri(meth)allylsilyl group substituted alkylaryl group and a tri(meth)allylsilyl substituted aryl group, which are bonded via an aryl group or alkyl group which may have a substituent, are exemplified. These spacer groups in the (meth)allylsilane compound intervene between the (meth)allylsilyl group, the halogenosilyl group and the polymerizable unsaturated group.

The (meth)allylsilane compound is, for example, represented by the following chemical formula (II)

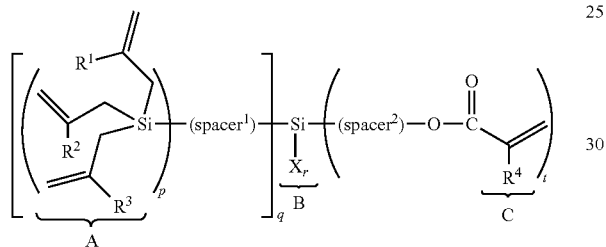

(II)

(In the formula (II), spacer$^1$ and spacer$^2$ may have a substituent and is the spacer group containing an alkyl group, an aryl group, an aralkyl group and/or a silyl group. Concerning p, q, r and t, p is 1 to 3, q is 1 to 3, r is 0 to 1, t is 0 to 3, and q+r+t=4, and at least two in q, r and t are a number of more than 1. $R^1$ to $R^3$ is a hydrogen atom or an alkyl group having a carbon number of 1 to 18, preferably hydrogen atom or a methyl group, $R^4$ is a hydrogen atom or a methyl group.) This (meth) allylsilane compound has at least two portions among three portions A-C. The Portion A is a (meth)allylsilyl group portion such as an allylsilyl group. The Portion B is a halogenosilyl group portion. And the Portion C is a polymerizable unsaturated group portion.

This (meth)allylsilane compound is, more specifically, represented by the following chemical formula (III).

(in the formula (III), alkyl$^1$ group, alkyl$^{1'}$ group, alkyl$^2$ group, and alkyl$^{2'}$ group may contain a substituent and are alkyl groups having a carbon number of 1 to 18 such as methylene or polymethylene; aryl$^1$ and aryl$^2$ may have a substituent and is a phenyl group such as phenylene; u1, v1, w1, u2, v2, w2 are 0 or 1; at least the number of any one of u1, v1 and w1 is counted as 1 and at least the number of one of u2, v2 and w2 is counted as 1; p, q, r, t, $R^1$ to $R^4$, X, A, B and C are the same as shown in formula (II)).

This (meth)allylsilane compound is represented, more specifically, by the following chemical formula (IV).

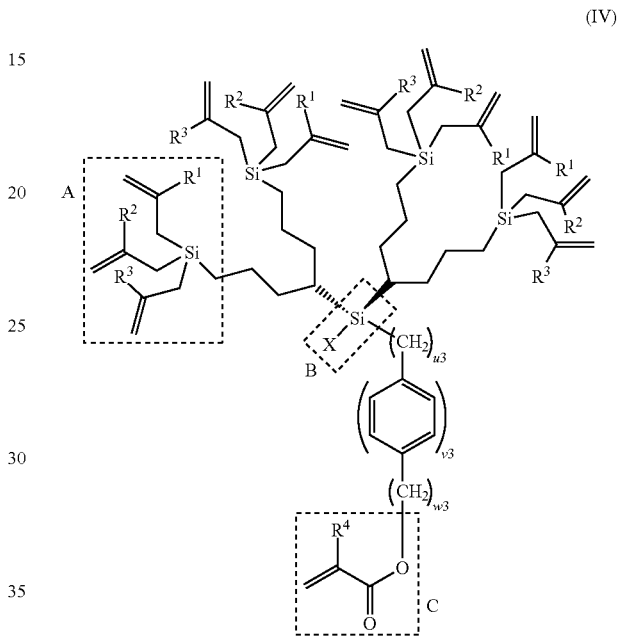

(IV)

(in the formula (IV), u3, v3, w3 are 0 or 1; at least the number of one of u3, v3 and w3 is counted as 1; $R^1$ to $R^4$, X, A, B and C are the same as described in the formula (II)).

The (meth)allylsilyl group of the (meth)allylsilane compound may be bonded to an aromatic compound selected from the group consisting of a biphenyl compound, a triarylamine compound and a carbazole compound. If necessary, aromatic compounds may be bonded to each other via the (meth)allylsilyl group.

To an allyl at the end of (meth)allylsilyl of the (meth) allylsilane compound, trihalogenosilane is reacted to introduce a trihalogenosilyl group, then to the halogeno group, a (meth)allylsilylgroup-containing organometallic compound is reacted to obtain a dendrimer-like group carbon-increased by (meth)allylsilyl.

(III)

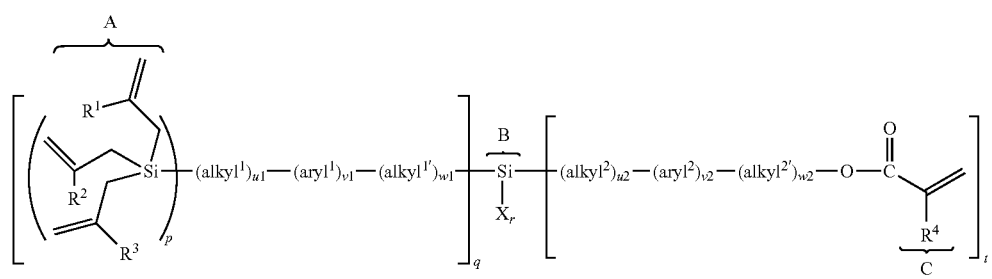

The silane coupling agent of the present invention may be formed from these (meth)allylsilane compounds or may be formed from another (meth)allylsilane compound derived by a further chemical reaction of the halogenosilyl group.

Such silane coupling agent may be, for example, a (meth) allylsilane compound having a (meth)allylsilyl group such as a mono-, di-, tri-(meth)allylsilyl group and having another reactive functional group which is formed from a halogenosilyl group bonded to the (meth)allylsilyl group via a spacer group in which an alkyl group, aryl group, aralkyl group and/or a silyl group is contained; or may be a (meth)allylsilane compound having a substituted silyl group, wherein the halogen of the halogenosilyl group is substituted with an alkyl group reacted with an alkyl metal compound, an aryl group reacted with an aryl metal compound, a hydroxyl group reacted with water or moisture, an alkoxy group reacted with an alkylalcohol, an aryloxy group reacted with an arylalcohol, a mercapto group reacted with hydrogen sulfide, an alkylthio group reacted with an alkylthiol, an arylthio group reacted with arylthio group, an amino group reacted with ammonia or a primary or secondary amine, a dehydrogenated sugar residue reacted with sugar having at least one hydroxide group that may be substituted with a substituent or protected by a protecting group, a hydrocarbon-based polyol dehydrogenated residue reacted with hydrocarbon-based polyols, an amino acid dehydrogenated residue reacted with amino acids which may be protected, a phosphoryl group reacted with phosphoric acids, a silyl group reacted with silanes, or a silyl oxy group reacted with silanol.

Another silane coupling agent may be a (meth)allylsilane compound in which a dehydrogenated residue of sugar, a dehydrogenated residue of hydrocarbon-based polyols or a dehydrogenated residue of amino acids is bonded to the (meth)allylsilyl group such as a mono-, di-, or tri-(meth) allylsilyl group to which a alkyl group or aryl group may be substituted. Such silane coupling agents can be obtained by reacting sugars, hydrocarbon-based polyols or amino acids with corresponding (meth)allylsilyl halides.

Another silane coupling agent may be a (meth)allylsilane compound: having at least any one of functional group selected from the group consisting of a reactive functional group formed from a (meth)allylsilyl group, another reactive functional group formed from a halogenosilyl group bonded to the reactive functional group via a spacer group which contains an alkyl group, an aryl group, an aralky group, and/or a silyl group, and a substituted silyl group in which a halogen of the halogenosilyl group is substituted with an alkyl group, an aryl group, a hydroxyl group, an alkoxy group, an aryloxy group, a mercapto group, an alkylthio group, an arylthio group, an amino group, a dehydrogenated residue of sugar, a dehydrogenated residue of a hydrocarbon polyol, a dehydrogenated residue of an amino acid, a phosphoryl group, a silyl group or a silyloxy group; and having a polymerizable unsaturated group connected directly or via a divergent spacer group which contains an alkyl group, an aryl group, an aralkyl group and/or an oxy group, to the functional group.

The silane coupling agent may include one or more such (meth)allylsilane compounds.

In the silane coupling agents, sugar that forms the (meth) allylsilane compound in which the dehydrogenated residues of the sugar are bonded to (meth)allylsilyl groups are preferably selected from the group consisting of monosaccharides or oligosaccharides, starches, cellulose, glycogens and cyclodextrins. More specifically, the monosaccharides such as glucose derivatives, mannose derivatives, xylose derivatives, galactose derivatives, etc.; the oligosaccharides that includes disaccharides to pentasaccharides such as sucrose derivatives, maltose derivatives, etc.; the starches which are polysaccharide derivatives containing a branched amylopectin structure and linear amylose structures having a linear structure in a specific ratio induced from a raw plant material; unsubstituted cellulose, regenerated cellulose such as rayon and cellophane, cellulose ether derivatives such as methyl cellulose and ethyl cellulose, glycosaminoglycan (mucopolysaccharide) such as hyaluronic acid, chitin, chitosan, chondroitin sulfate, cellulose ester derivatives such as nitrocellulose and cellulose acetate; the glycogens such as glycogen, etc.; the hexa to octa saccharides such as cyclodextrins such as α-cyclodextrin derivatives, β-cyclodextrin derivatives, γ-cyclodextrin derivatives, etc. can be exemplified.

In the silane coupling agents, polyols that form the (meth) allylsilane compound in which dehydrogenated residues of hydrocarbon-based polyols are bonded to the (meth)allylsilyl groups, have unprotected polyvalent or plural free hydroxyl groups, or some of the hydroxyl groups which are protected and have at least one free hydroxyl group, and further may have a substituent. Polyol derivatives having unprotected and unsubstituted hydroxyl groups are a linear, branched and/or cyclic saturated or unsaturated structure. As such polyol derivatives, aliphatic alcohol derivatives having polyvalent hydroxyl groups or aromatic derivatives having a polyvalent hydroxyl group are exemplified.

These saccharides and polyol derivatives may have unsubstituted and unprotected hydroxyl groups. Some of these hydroxyl groups are protected so as to deprotect the protected condition or so as not to deprotect the protected condition.

In the silane coupling agents, as amines and amino acids which form (meth)allyl silane compounds in which dehydrogenated residue groups of amines or amino acids are bonded to the (meth)allylsilyl groups, primary amines such as aniline; secondary amines such as N,N'-diphenylamine; an optically active amino acids such as threonine; or amino acids of one side optically active predominance or racemic mixture can be exemplified.

As substituents that they may contain, halogen atoms, alkyl groups or alkyloxy groups having a carbon number of 1 to 20, nitro groups, cyano groups, aralkyl groups or aryl groups having a carbon number of 1 to 24, can be exemplified. These may be used in singular or multiple.

As protective groups for sugar, for example, benzyl groups, isopropylidene groups, methyl groups, p-methoxybenzyl groups, tert-butyl groups, methoxymethyl groups, 2-tetrahydropyranyl groups, acetyl groups, pivaloyl groups, benzoyl groups, trimethylsilyl groups, tert-butyldimethylsilyl groups, triisopropylsilyl groups, tert-butyl diphenyl silyl groups are exemplified.

In the silane coupling agent, the (meth)allylsilane compound may have a catalytic functional groups, conjugated functional groups and molecular recognition functional groups. The catalytic functional groups are phosphine-containing functional groups and/or hetero ring-containing functional groups. The conjugated functional groups are carbazole ring-containing functional groups, polyene-containing functional groups, polyyne-containing functional groups and/or polyarene-containing functional groups. The molecular recognition functional groups are optically active site-containing functional groups such as optically active binaphthyl groups, optically active amino groups and optically active acid groups.

The (meth)allylsilane compound can be produced as follows. The (meth)allylsilyl group can be, for example, produced by reacting tetra alkoxysilane or trialkoxysilane with Grignard reagent such as allyl magnesium bromide, (meth) allylsilyl group-containing alkyl magnesium halide or (meth)

allylsilyl group-containing arylmagnesium halide etc. When one alkoxy group left in the silyl group is halogenized with a halogenating agent such as triphenylphosphine dihalide, therefore a (meth)allylsilane compound is obtained. If necessary, polymerizable unsaturated group is introduced.

The (meth)allylsilane compound may be amplified by the (meth)allylsilyl group, through a reaction which trihalogenosilane is added to the end of the (meth)allylsilyl group of the (meth)allylsilane compound, and then, organic metal compound (ex. Grignard reagent) such as allyl magnesium halide, (meth)allylsilyl group-containing alkyl or arylmagnesium halide may further reacted to its halogenosilyl group to amplify the (meth)allylsilyl group.

The silane coupling agent of the present invention preferably contains this (meth)allylsilane compound as an active silane coupling ingredient. The silane coupling agent may only have this tri(meth)allylsilane as an active silane coupling agent, but alkoxysilane having alkyl chain of carbon number of 1 to 6 such as 1,2-bis(trialkoxysilyl)ethane; polycarboxylic acid halide such as oxalyl chloride, malonyl chloride, succinyl chloride and terephthaloyl chloride; poly carboxylic acid anhydride such as tartaric acid anhydride, phthalic anhydride and maleic anhydride may be coexisted as silane coupling agents.

The functional material is ether-bonded by silane coupling via at least some surface hydroxide groups that are exposed on the base material.

In another illustrative embodiment of functional material, another silane coupling agent having an alkyl group, a partial fluoroalkyl group, a perfluoro alkyl group and/or an aryl group, and having a trialkoxysilyl group, a dialkoxyallylsilyl group, an alkoxydiallylsilyl group and/or a triallylsilyl group, each of which may have substituent, are ether-bonded furthermore on the base material via the surface hydroxy groups through silane coupling. Thus, the scratch resistance property can be further improved. This functional material can be obtained by immersing a base material into a composition obtained by solving another silane coupling agent into a solvent such as toluene, acetonitrile, acetone, etc. so as to get solution of 0.1 to 10% concentration, or by applying the composition on the base material, and then heated at a temperature of 40 to 200° C., forming a new silylether bonding.

The base materials of functional materials may be plane shapes such as plates, film, sheets or 3-dimensional shapes such as pillars or solids, and may be made of glass base materials, metal base materials, ceramics base materials, resin base materials such as thermosetting resins and thermoplastic resins, liquid crystal panels. Due to the presence of a free hydroxyl group of the polyol derivatives that are comprised of (meth)allylsilane compound of the silane coupling agent, anti-fogging property can be developed because the functional materials have an affinity to water such as moisture or aqueous droplets.

As another illustrative embodiment of the functional materials, the base material has, for example, a granular or powdery shape having a weight average diameter or volume average diameter of 1 μm to 1 mm. For example, glass particles, silica gel particles, alumina particles, metal particles, ceramics particles, resin particles, and modified particles which the surface of any of them are chemically modified by coating with metals, metal oxides or resins etc. Such functional materials are derived from polyol derivatives which are comprised of (meth)allylsilane compounds in the silane coupling agents. The functional materials can have hydrophilic property which is induced from hydrophilicity of the free hydrophilic group; hydrophobicity which is induced from a hydrophobic group; absorptive property which is induced from the hydrophilic group and the hydrophobic group; stereospecifity which is induced from configuration. According to those functionalities, the functional material may be a carrier used in column chromatography which is used for elution or separation of a solute such as a suspected substance to be analyzed by high-performance liquid chromatography or a crude composition to be purified by liquid chromatography.

The surface hydroxyl group of the base materials may be one which is already originally exposed, one which is generated by surface treatment with an acidic solution treatment of immersing or spraying strong acid such as concentrated or diluted sulfuric acid, concentrated or diluted hydrochloric acid, or concentrated or diluted nitric acid, or peroxide such as hydrogen oxide at the time or before the treatment, or another one which is generated by surface treatment with alkaline aqueous solution, ultra violet light irradiation, a corona discharge treatment, or a plasma treatment.

The functional material is prepared, for example, by the following steps; tri(meth)allylsilyl group of (meth)allylsilane compound in the silane coupling agent reacts through silane-coupling reaction with the surface hydroxyl group on the base material so that propene is eliminated from the system to become di(meth)allylsilyl group; further if necessary, another surface hydroxyl group of the same substrate reacts through silane-coupling reaction to become mono(meth)allylsilyl group; and if necessary again, another surface hydroxyl group of the same base material reacts through silane-coupling reaction so that some of or all of this tri(meth)allylsilyl groups are ether-bonded through or via the surface hydroxyl group of the base material.

As mentioned above, silicon atoms of tri(meth)allylsilyl group di(meth)allylsilyl groups of the (meth)allylsilane compound in the silane coupling agents are ether-bonded directly to oxygen atoms of the surface hydroxyl groups of the base materials.

In addition, some or all of each (meth)allylsilyl groups in the tri(meth)allylsilyl group and the di(meth)allylsilyl group may be hydrolyzed under an acidic condition to become a silanol group (SiOH group). The silanol groups react with: silicon atoms of tri(meth)allylsilyl groups and di(meth)allylsilyl groups of coexisting other (meth)allylsilane compound molecules; or silanol groups which are converted as well; or alkoxysilyl groups of coexisting tetra alkoxysilane, to condensate or polycondensate. But all of these silanol groups, (meth)allylsilyl groups and alkoxysilyl groups are not completely condensated or polycondensated. At least some amounts of them are remained unreacted according to reaction conditions such as acid strength, temperature, reaction time etc. Such groups condensate with surface hydroxyl groups of the base materials, for example, surface hydroxyl groups or silanol groups of, for example, glass base materials, glass particles or silica gel particles, to form a new siloxane bond (—Si—O—Si—). At last, the (meth)allylsilane compounds in the silane coupling agents are functionally transformed and then supported on the base material.

When at least one free hydroxyl group derived from polyol derivative in the (meth)allylsilane compound of the functional material is deprotected as needed and exposed to the air, hydrophilicity is increased and functionality such as anti-fogging property, separation property in column chromatography, etc. are improved.

These functional materials can be produced as follows. Silane coupling agents are attached using applying, spraying, immersing or printing methods on a base material on which surface hydroxyl groups are exposed to the air. And then a step of the silane coupling reaction using the so-called sol-gel method is carried out. In the sol-gel method, the sol state, which fine particles of the silane coupling agent are dispersed in a solution, is changed to a gel state and then to the solid state. During sol-gel method, the silane coupling reaction is carried out to form ether bonds by silane coupling reaction between tri(meth)allylsilyl group and di(meth)allylsilyl group of the (meth)allylsilane compound in the silane coupling agent via the surface hydroxyl group, obtaining the functional material.

Silane coupling reaction can be carried out after a silane coupling agent is treated with acid aqueous solution such as diluted hydrochloric acid, diluted sulfuric acid, diluted nitric acid, diluted acetic acid so as to change some or almost or all of tri(meth)allylsilyl group and di(meth)allylsilyl group of (meth)allylsilane compound into the silanol group. A silane coupling reaction may be carried out after functional group-changing step in which the siloxy group is formed by treating the silane coupling agent with an acid aqueous solution to change the silanol group into siloxy group and then is reacted through a condensation or polycondensation reaction with tetra-alkoxysilane, or after functional group changing step in which another siloxy group is formed by polycondensation of the silanol group, siloxy group or alkoxysilyl group using concentrated sulfuric acid. Silane coupling reaction may be carried out after an oligomer changing step in which the silane coupling agent is esterified with polycarboxylic acid anhydride or polycarboxylic acid halide. The treating step with polycarboxylic acid anhydride or polycarboxylic acid halide is preferably carried out in an anhydrous organic solvent, specifically a water-insoluble organic solvent such as methylene chloride, toluene, etc. If necessary, a protecting group of the polyol derivatives is preferably deprotected so as for the free hydroxy group to be exposed to the air.

The functional materials are utilized as: anti-reflective materials and anti-fogging materials used for livingware, electronic or electric equipments to be avoiding cloudiness or preventing reflection such as glass windows, glasses, etc.; carriers for column chromatography which is used to separate subjects by affinity column chromatography and high pressure column chromatography to isolate or analyze test substances precisely and surely; electronic materials such as charge transport materials of the electrophotographic photoreceptors or hole transport materials of organic electroluminescence elements or the like; catalysts for organic synthesis, particularly as asymmetric catalysts which are used repeatedly by recovering; or material for enhancing surface protection properties to improve oil repellency and lipophilicity, abrasion resistance and water repellency.

Second preferred embodiment of the present invention is as follows.

The (meth)allylsilane compound is characterized in that a (meth)allylsilyl group-containing alkyl group or (meth)allylsilylalkyl group-containing aralkyl group, which may have a substituent, is covalently bonded by a chemical bonding group directly or indirectly to a dehydrogenated residue of an amino group of an amino group-containing compound.

As a (meth)allylsilyl group of a (meth)allylsilyl group-containing alkyl group of the (meth)allylsilane compound, mono(meth)allylsilyl group, di(meth)allylsilyl group and tri(meth)allylsilyl group are exemplified, but tri(meth)allylsilyl group, which has a larger number of allyl group that acts as a reactive functional group, is more preferable. However, mono-(mono-, di-, or tri-(meth)allylsilyl)alkyl group, bis-(mono-, di-, or to tri-(meth)allylsilyl)alkyl group, tris-(mono-, di-, or tri-(meth)allylsilyl)alkyl group may be used. Exemplified are the alkyl group of this (meth)allylsilyl group-containing alkyl group which is a saturated or unsaturated linear, branched, or cyclic alkyl group having a carbon number of 1 to 20, preferably 3 to 6, which may have a substituent. The alkyl group of the (meth)allylsilyl alkyl group-containing aralkyl group is the same as described above. As the aralkyl group, an arylalkyl group can be exemplified which is like a benzyl group or phenethyl group having a carbon number of 7 to 8, which may have a substituent.

In the (meth)allylsilane compound, the (meth)allylsilyl group-containing alkyl group or (meth)allylsilyl alkyl group-containing aralkyl group may be directly bonded to a dehydrogenated residue of amino group of amino group-containing compound. For example, (meth)allylsilyl group-containing alkyl group or (meth)allylsilylalkyl group-containing aralkyl group is amino-bonded to a free amino group (—$NH_2$, —NH—) of a free amino group-containing compound which is a primary or secondary amine. Such direct amino bonding is formed, for example, when a free amino group of free amino group-containing compound is reacted, in a nucleophilic substitution manner, to halide or tosylate or mesylate of (meth)allylsilyl group-containing alkyl group or, (meth)allylsilyl alkyl group-containing aralkyl group. In addition, a (meth)allylsilyl group-containing alkyl group or a (meth)allylsilyl alkyl group-containing aralkyl group may be connected, indirectly, using an amino group of an amino group-containing compound via a carbamic acid ester group or amide group. Such indirect connection can be formed, for example, after (meth)allylsilyl group-containing alkylalcohol or (meth)allylsilylalkyl group-containing aralkyl alcohol is reacted with triphosgene ($CCl_3$—O—CO—$CCl_3$), then amino group-containing compound is reacted thereto.

In (meth)allylsilane compound, a (meth)allylsilyl group-containing tertiary alkyl group derived from 1,1-bis{3-(triallylsilyl)propyl}ethanol and has a chemical structure which just looks like a tert-butoxycarbonyl group (Boc group) and a (meth)allylsilylalkyl group-containing aralkyl group derived from 4-{3-(triallylsilyl)propyl)}benzylalcohol and has a chemical structure which just looks like a benzyloxycarbonyl group (Cbz group), and connects to form a carbamic acid ester group as if it protects an amino group of an amino group-containing compound.

Concerning an amino group-containing compound, if it has at least a group that can be —NH— group, any compound can be used. The amino group may be unprotected and unsubstituted one. The amino group may be formed into a salt. If necessary, it can be formed into a deprotectable or undeprotectable amide, and it may have a substituent. It may be hydrocarbon base amines. When the amino group-containing compound is amino acids, it may be a carboxylic acid ester.

More specifically, primary amines such as benzylamines; secondary amines such as diisopropylamines; amino acids of optically active substance such as (S)-threonine, and an optically active compound or a racemic substance can be exemplified as the amino group-containing compound.

Among them, the amino group-containing compounds are preferably amino acids which may have substituents and protective groups and may be salts thereof.

Substituents that they may have, are halogen atoms, alkyl groups or alkyloxy groups having a carbon number of 1 to 20, nitro groups, cyano groups, aralkyl groups or aryl groups having a carbon number of 1 to 24. They may be used in singular or multiple.

As protecting groups of sugar, for example, benzyl groups, Boc groups, Cbz groups, fluorenyl methoxycarbonyl groups (Fmoc groups), 2,2,2-trichloro ethoxycarbonyl groups (Troc groups), allyloxy carbonyl groups (Alloc groups), 2-nitrobenzene sulfonyl groups (Ns groups), phthaloyl groups (Pht groups) can be exemplified.

This (meth)allylsilane compound can be produced, for example, as follows. A trihalogenosilyl group-containing compound obtained by reacting the terminal of an olefin compound and a trihalogenosilane is reacted with Grignard reagent such as allylmagnesium bromide, etc. Thus tri(meth) allylsilyl group is formed. After that, if necessary, carbon-carbon or oxygen-carbon covalent-bond-formable reactive functional group is changed or introduced into an alcohol precursor, so that the alcohol precursor represented by the following chemical formula (V) is prepared.

(in the formula (V), -A- is a spacer selected from an alkyl group and alkylaralkyl group.) After this alcohol precursor is reacted with a reactive compound such as triphosgene to obtain a halogeno formic acid ester which is then reacted with amino group-containing compound, obtaining a (meth)allyl-silane compound having a carbamic acid ester group.

The silane coupling agent of the present invention preferably contains the (meth)allylsilane compound as a silane coupling active ingredient, As the silane coupling agent, only this (meth)allylsilane compound may be contained as the silane coupling active ingredient. However, tetra alkoxysilane having an alkoxyl group having 1 to 6 carbon atoms such as tetra ethoxysilane; polycarboxylic acid halide such as oxalyl chloride, malonyl chloride, succinyl chloride, tereph-thaloyl chloride; poly-carboxylic acid anhydride such as tartaric acid anhydride, phthalic anhydride, maleic anhydride, etc. may be coexistingly contained as a silane coupling component.

In the functional material of the present invention, silane coupling agent is ether-bonded via at least some surface hydroxyl groups through silane coupling on the base material on which the surface hydroxyl group is exposed to the air.

The functional material has a base material having planar shapes of a plate-like shape, a film-like shape or a sheet-like shape, or tridimensional shapes such as a pillar shape and a solid-like shape etc., and is a glass base material, a metal base material, a ceramics base material or a resin base material such as a thermoplastic resin, a thermo-setting resin, a liquid crystal panel, etc. Due to a hydrophilic functional group such as a carboxyl group or an amino group derived from an optically active amino acid or an amino group-containing compound that comprises a (meth)allylsilane compound in the silane coupling agent, the functional material has affinity to water drops, moisture or water so that it can be used as an anti-fogging material having an anti-fogging property.

In another illustrative embodiment of the functional material, its base materials are particles having a powdery or granular shape, with weight average particle size or volume average particle size of 1 μm to 1 mm, such as glass particles, silica gel particles, alumina particles, metal particles, ceramics particles, resin particles, or particles having surfaces which are coated or chemically modified with metal, metal oxide or resin. The functional material has hydrophilicity induced from a carboxy group and an amino group derived from an optically active amino acid such as an amino group-containing compound that composes (meth)allylsilane compound in the silane coupling agent, hydrophobicity induced from hydrophobic group thereof, adsorptive property induced from hydrophilicity and hydrophobicity and/or stereospecificity induced from the absolute structure of optically-active substance such as three-dimensional configuration. Such functional material can be used as a column chromatography carrier which is used to elute and/or separate a subject to be analyzed in a high-performance liquid chromatography, or a crude composition to be purified by a liquid chromatography.

The base materials having surface hydroxyl groups which are originally exposed to the air may be used. The surface hydroxyl groups may be formed by surface treatment of immersing or splaying with strong acid such as diluted or concentrated hydrochloric acid, diluted or concentrated sulfuric acid or diluted or concentrated nitric acid, or peroxides such as hydrogen peroxide before or at the time of silane coupling treatment. The surface hydroxyl groups may be formed by an alkaline aqueous surface treatment, an ultraviolet irradiation treatment, a corona discharge treatment, a plasma treatment, etc.

For example, when a tri(meth)allylsilyl group of (meth) allylsilane compound in the silane coupling agent is reacted to the surface hydroxyl group on the base material of the functional material through the silane coupling reaction, propene is eliminated and di(meth)allylsilyl group is generated. Further, if necessary, silane coupling reaction is carried out to another surface hydroxyl group of the same base material, mono(meth)allylsilyl group is produced. Further, if silane coupling reaction is carried out to another surface hydroxyl group of the same material, some or all of the tri(meth) allysilyl groups are ether bonded via the surface hydroxyl group of the base material.

The tri(meth)allylsilyl group, di(meth)allylsilyl group or mono(meth)allylsilyl group of (meth)allylsilane compound in the silane coupling agent can be directly ether-bonded via the oxygen atom of the surface hydroxyl group to the silicon atom derived from (meth)allylsilane compound.

In addition, each (meth)allylsilyl group of the tri(meth) allysilyl group, di(meth)allylsilyl group or mono(meth)allyl-silyl group may be all or partially hydrolyzed to be a silanol group (SiOH group). The silanol groups is reacted to; silicon atoms of tri(meth)allylsilyl group, di(meth)allylsilyl group or mono(meth)allylsilyl group of a other coexisting (meth)allyl-silane compound; a silanol group which is changed as well; or the alkoxysilyl group of an coexisting tetra alkoxysilane, performing condensation or polycondensation reaction. However, these silanol groups, (meth)allylsilyl groups and alkoxysilyl groups, are not completely condensated or poly-condensated, so that at least some of them are still remained as they are according to the reaction environment such as acid strength, temperature, reaction time, etc. They condensate with the surface hydroxyl groups of the base materials such as the surface hydroxyl groups (or silanol group) of the base materials, for example, glass base materials, glass particles or silica gel particles, thereby generating new siloxane bonds (—Si—O—Si—). At last (meth)allylsilane compounds in the silane coupling agents are transformed into functional groups and are supported on the base materials.

Such functional materials are prepared as follows. The silane coupling agents are coated using applying, spraying, immersing or printing method on the base materials of which surface hydroxyl groups are exposed to the air. Silane coupling reactions are carried out by so-called sol-gel method in which fine particles of the silane coupling agents are at first dispersed in solution (sol state) are changed into a gel state and at last changed into a solid state through the step of the silane coupling reaction. Via the surface hydroxyl groups, tri(meth)allylsilyl groups, di(meth)allylsilyl groups or, mono (meth)allylsilyl groups of the (meth)allylsilane compound in the silane coupling agents perform silane-coupling reaction, to form ether bond, giving the functional material.

The silane coupling agents are treated with acid aqueous solution such as dilute hydrochloric acid, dilute sulfuric acid, dilute nitric acid, dilute acetic acid. Some or almost all or completely all of the tri(meth)allylsilyl groups, di(meth)al-lylsilyl groups and mono(meth)allylsilyl groups as functional groups of (meth)allylsilane compound are transformed into silanols. Then silane coupling reaction may be carried out. The silane coupling reaction may be carried out after a step in which silane coupling agent is treated with an acid aqueous solution to generate a silanol group, and then condensation or polycondensation reaction is carried out with tetraalkoxysilane so that silanol group is changed into a siloxy group, or silane coupling reaction may be carried out after a step in which silanol group, siloxy group and alkoxysilyl group as functional group are polycondensed using concentrated sulfuric acid to obtain another siloxy group. Silane coupling reaction step may be carried out after a step in which silane coupling agent is esterified with polycarboxylic acid halide or polycarboxylic acid anhydride to obtain an oligomer. The treatment with polycarboxylic acid halide or polycarboxylic acid anhydride is preferably carried out in anhydrous organic solvent, particularly, in water insoluble solvent such as methylene chloride and toluene. If necessary, the protective group derived from amino group-containing compound may be deprotected.

Thus obtained functional materials are used as anti-fogging materials for livingware, electronic and electric devices which should avoid cloudiness caused by steam or moisture, or used as carrier for high-performance liquid chromatography or affinity column chromatography.

The preferred third embodiment of the present invention is as follows.

The perfluoro group-containing (meth)allylsilane compound of the present invention is a compound which tri(meth)allylsilyl group that may have a substituent and a linear, branched and/or cyclic perfluoro group are bonded via a spacer group.

As the perfluoro group, a saturated or unsaturated linear, branched and/or cyclic structure having an alicyclic or aromatic ring having a carbon number of 1 to 24 is exemplified. More preferably, a non-cyclic linear and/or branched perfluoroalkyl group having a carbon number of 1 to 24, preferably 1 to 18, more preferably 3 to 18, still more preferably 3 to 12; a cyclic perfluorocyclo alkyl group having a carbon number of 3 to 24, preferably 3 to 18, more preferably 3 to 12 which is a linear and/or branched group; a linear and/or branched non-cyclic perfluoro alkenyl group having a carbon number of 2 to 24; a cyclic perfluorocycloalkenyl group having a carbon number of 3 to 24 linear group and/or branched group; or a perfluoroaralkyl group having a carbon number of 7 to 24 can be exemplified. As preferable embodiments, linear, branched, or cyclic, saturated or unsaturated perfluoro groups represented by $C_mF_{2m+1}$— (m is 1 to 18, preferably 6 to 12) and $C_mF_{2m-1}$— or $C_mF_{2m-3}$— (m is 2 to 18, preferably 6 to 12) are exemplified.

Among them, more preferably $C_mF_{2m-1}$— is a perfluoro group represented by the following chemical formula (I).

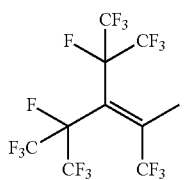

(I)

If the spacer group has a carbon number of 1 to 36, preferably 1 to 24, more preferably 3 to 24, any alkylene group that has a linear and/or branched chain that may have a substituent can be used. A linear and/or branched alkylene ether group for example —O—$(CH_2)$—, —$(CH_2)_n$—O— (n is 1 to 36, preferably 1 to 24, more preferably 3 to 24) that may have a substituent, which may contain these single or plural alkylene groups and alkylene ether groups, can be used. When a plurality of alkylene ether groups are contained, molecular weight of polyalkylene glycol corresponding to it is 88 to 50,000, preferably a number average molecular weight or a weight average molecular weight is 200 to 50,000. The substituent may be used in singular or multiple. For example, a hydroxyl group and a (meth)acrylic acid ester group, which a dehydrogenated residue of the hydroxyl group is bonded to the (meth)acryloyl group such as an acryloyl group and a methacryloyl group, are exemplified.

Such perfluoroalkyl group-containing (meth)allylsilane compound, for example, is represented by the following chemical formula.

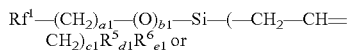

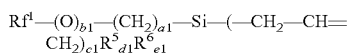

($Rf^1$ is a non-cyclic perfluoroalkyl group having a carbon number of 1 to 24, preferably 1 to 18, more preferably 3 to 18, still more preferably 3 to 12; a cyclic perfluorocyclo alkyl group may be a linear and/or a branched group having a carbon number of 3 to 24, preferably 3 to 18, more preferably 3 to 12; a non-cyclic perfluoro alkenyl group which has a linear and/or a branched chain having a carbon number of 2 to 24; a cyclic perfluoro cycloalkenyl group which has a linear and/or a branched chain having a carbon number of 3 to 24; or a perfluoro aralkyl group having a carbon number of 7 to 24, a1 is 1 to 36, preferably 1 to 24, more preferably 3 to 24, b1 is 0 to 1, c1 is 1 to 3, d1 and e1 are 0 to 1, c1+d1+e1=4, $R^5$ and $R^6$ are carbon number of 1 to 24 and a linear, a branched and/or a cyclic alkyl.)

or

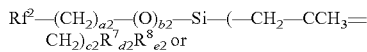

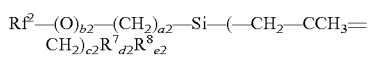

($Rf^2$, a2, b2, c2, d2, e2, c2+d2+e2, $R^7$ and $R^8$ are the same as of the f1, a1, b1, c1, d1, e1, c1+d1+e1, $R^5$ and $R^6$ described above.)

Another perfluoro group-containing (meth)allylsilane compound is, for example, represented by the following chemical formula;

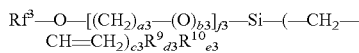

($Rf^3$ is the same as $Rf^1$, a3 is 2 to 12, preferably 2 to 4, more preferably 2, b3 is 1, f3 is the number by which the molecular weight of poly(alkyleneoxy) group represented by the following formula of HO—$[(CH_2)_{a3}$—$(O)_{b3}]_{f3}$—H is 88 to 50,000, preferably the number average molecular weight or weight average molecular weight is 200 to 50,000, c3, d3, e3, c3+d3+e3, $R^9$ and $R^{10}$ are the same as the c1, d1, e1, c1+d1+e1, $R^5$ and $R^6$)

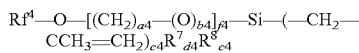

($Rf^3$ is the same as $Rf^1$, a4 is 2 to 12, preferably 2 to 4, more preferably 2, b4 is 1, f4 is the number by which the molecular weight of poly(alkyleneoxy) group represented by the following formula of HO—$[(CH_2)_{a4}$—$(O)_{b4}]_{f4}$—H is 88 to 50,000, preferably the number average molecular weight or weight average molecular weight is 200 to 50,000, c4, d4, e4, c4+d4+ e4, $R^7$ and $R^8$ are the same as the c1, d1, e1, c1+d1+e1, $R^1$ and $R^2$)

Instead of tri(meth)allysilyl group, alkyl[di(meth)aryl]silyl group or dialkyl[(meth)allyl]silyl group having a carbon number of 1 to 24 linear, branched and/or cyclic alkyl such as methyl group may be used. Here, if the (meth)allyl has an allyl carbon skeleton, it may have a substituent.

A process of producing the perfluoro group-containing (meth)allylsilane compound is as follows: to a perfluoroalkyl containing perfluoroalkyl-1,2-epoxypropane having carbon number of 1 to 24 linear, branched and/or cyclic chain, an organic metal compound (ex. a Grignard reagent) of any one of a tri(meth)allylsilyl alkylene metal compound containing alkylene having carbon number of 1 to 36, preferably 1 to 24 linear, branched and/or cyclic chain, an alkyl[di(meth)allyl] silylalkylene metal compound or dialkyl[(meth)allyl]silyl alkylene metal compound containing alkylene having a carbon number of 1 to 24 linear, branched and/or cyclic alkyl and a carbon number of 1 to 36 preferably 1 to 24 linear, branched and/or cyclic alkylene is reacted to be ring-opened, in order to obtain a desired product. If necessary, (meth)acrylic acid anhydride or (meth)acrylic acid may be reacted with a newly generated hydroxyl group to change the hydroxyl group into a (meth)acryloyloxy group.

Another process for producing a perfluoro group-containing (meth)allylsilane compound is as follows; a hexafluoropropene trimer and the organic metal compound are reacted nucleophilicly to substitute the fluoro carbon of the fluoroethylene of the hexafluoropropene trimer.

Still another process to produce a perfluoro group-containing (meth)allylsilane compound is as follows; to a fluoro carbon of the fluoroethylene group of the hexafluoropropene trimer, a hydroxyl group of epoxy group-containing alcohol such as glycidol or glycerin diglycidyl ether is reacted to obtain an etherized substitution to which, as the same process described above, an organic metal compound is reacted to carry out ring-opening of the epoxy ring, to obtain a perfluoro group-containing (meth)allylsilane compound. If necessary, (meth)acrylic acid anhydride or (meth)acrylic acid may be reacted with a newly generated hydroxyl group to change the hydroxyl group into a (meth)acryloyloxy group.

The coating composition of the present invention is comprised of the (meth)allylsilane compounds, particularly, perfluoro group-containing (meth)allylsilane compounds, and if necessary, vehicles such as methyl isobutyl ketone, methyl ethyl ketone, and acetone, and additives such as acid catalysts. The coating composition is directly attached onto various base materials such as silica particles, glass plates, metal plates or resin films to bond the perfluoro group-containing allylsilane compounds to functional groups on the base material surfaces.

Another coating composition of the present invention is prepared as following procedures. A perfluoro group-containing (meth)allylsilane compound, and particles such as glass particles, silica particles, alumina particles, metal particles, ceramics particles, resin particles, surface chemically modified particles thereof, especially silica particles are preliminarily stirred with heat if necessary. A hydroxyl group derived from silanol on the surface the silica particles is chemically bonded to the perfluoro group-containing (meth) allylsilane compound preliminarily. And then a binder such as a coating resin illustrated by polyfunctional acryl resin raw material or urethane acrylate, medium and additives exemplified previously are included if necessary, to prepare the coating composition. This coating composition is coated on various base materials such as glass plates, metal plates, resin film, etc. If necessary, they are heated or irradiated with active energy ray such as ultra violet ray or electron beam, to cure to form the coated layer.

The base material, on which the coating composition is applied, may originally have surface hydroxyl groups that are exposed to the air. Surface hydroxyl groups may be formed by surface treatment of immersing or splaying with strong acid such as diluted or concentrated hydrochloric acid, diluted or concentrated sulfuric acid or diluted or concentrated nitric acid etc., or peroxides such as hydrogen peroxide. Surface hydroxyl groups may be formed by surface treatment with alkaline aqueous solution, ultraviolet irradiation, corona discharge treatment, plasma treatment, etc.

The base material, on which such coating composition including no particles is coated, is a particle of powder or granule having a weight average particle diameter or volume average particle diameter of 1 nm to 1 mm. Glass particles, silica particles such as colloidal silica particles, fumed silica particles, alumina particles, metal particles such as iron powder or aluminum powder, ceramics particles, resin particles such as acrylic resin particles, or resin modified particles of which surface of above-mentioned particles is treated by coating, can be used. As the base material on which the particle-containing coating composition, glass base materials, metal base materials, ceramics base materials, resin base materials, resin films, resin sheets, or other materials of which surface of above-mentioned materials is treated by coating, can be used.

In the coating materials of the present invention, an active functional group on the surface of the base materials, for example, hydroxyl group of the surface of the base material is reacted with tri(meth)allylsilyl group of perfluoro group-containing (meth)allylsilane compound, so that propene is eliminated and di(meth)allylsilyl group is generated. Further, if necessary, silane coupling reaction is carried out to another surface hydroxyl group of the same base material, mono(meth)allylsilyl group is formed. Still further, if necessary, when silane coupling reaction is carried out to another surface of the same base material, some or all tri(meth)allylsilyl group is/or are ether-bonded via the surface hydroxyl group of the base material. Di(meth)allylsilyl group or mono(meth) allylsilyl group of perfluoro group-containing (meth)allylsilane compound has a similar reaction mentioned above.

As mentioned above, tri(meth)allylsilyl group, di(meth) allylsilyl group or mono(meth)allylsilyl group of the perfluoro group-containing (meth)allylsilane compound is reacted with a silicon atom derived from the compound and directly ether-bonded via, for example, an oxygen atom of a hydroxyl group which is an active functional group on the surface of the base material.

All or some of the (meth)allylsilyl groups in tri(meth) allylsilyl group or di(meth)allylsilyl groups or mono(meth) allylsilyl groups may be hydrolyzed under an acid environment and changed into a silanol group (SiOH group). The silanol group reacts to a silicon atom of tri(meth)allylsilyl group, di(meth)allylsilyl group and mono(meth)allylsilyl group of other coexisting (meth)allylsilane compound molecules or a silanol group which is converted therefrom as well as above-mentioned, to perform condensation or polycondensation reaction. However, these silanol groups, (meth)allylsilyl groups or alkoxy silyl groups are not all condensed or polycondensated under a reaction condition such as acid strength, temperature, reaction time, so that at least some of them are remained unreacted. Such remaining groups are reacted condensationally with the surface hydroxyl groups, silanol groups of the base material such as glass base materials, glass particles, silica particles, to form a new siloxane bond (—Si—O—Si—), and at last, perfluoro group-containing (meth)allylsilane compounds are functional-group-transformed and supported on the base material.

Such coating materials are, for example, manufactured as follows.

A coating composition including no particle is applied by coating, spraying, immersing or printing method on the base material on which surface hydroxyl groups are exposed to the air. Then a sol-gel method in which the sol state in which (meth)allylsilane compound such as perfluoro group-containing (meth)allylsilane compound is dispersed in a solution is changed into the gel state and then to a solid state, silane coupling and/or curing reactions are carried out. Through or via the surface hydroxyl group of any base materials such as glass particles, silica particles, alumina particles, metal particles, ceramics particles, resin particles, chemically surface modified particles, silica plates, glass plates, metal plates, ceramics plates, resin plates, films of resin, plates of resin, etc., tri(meth)allylsilyl group or di(meth)allylsilyl group or mono(meth)allylsilyl group of the perfluoro group-containing (meth)allylsilane compound is reacted through silane coupling reaction to form an ether bonding, preparing the coating materials. In a case that the base materials are particles, a thin layer is formed by multiple progresses of the sol-gel method and silane coupling reaction. In a case that the base materials are plates, film or sheets, in particular, a thin layer is formed by coating using a coating agent, and then ultraviolet irradiation to be cured.

The coating composition containing filler particles modified with a perfluoro group-containing (meth)allysilane compound which is bonded to the functional groups of the particle's surface and a coating resin such as urethane acrylate or a polyfunctional acryl resin raw material, is surface coated and modified on the base materials such as glass plates, metal plates, ceramics plates, resin plates, resin film, resin sheets, and then cured, if necessary, obtaining a coating material having a cured coated resin.

In these coating materials, a perfluoro group-containing (meth)allylsilane compound is strongly attached and bonded to the base material at the surface thereof by chemical bonding. Therefore delamination is hardly occurred. Further, the perfluoro groups on the surface of the cured polymer are exposed to the air, lowering the surface energy, so that the coated layers exhibit excellent water and oil repellency. The coating materials can be used for protection of base materials using its anti-scratch property.

EXAMPLES

The (meth)allylsilane compounds, their silane coupling agents and Examples of functional materials of the present invention will be explained below with reference to Examples.

Example 1

(1.1) Under a nitrogen atmosphere, to 1,4-dibromobenzene (1) (15 g, 15.9 mmol), cyclopentyl methyl ether (CPME) (90 ml) was added and cooled to around −10° C. using salt ice, tetrahydrofuran (THF) solution ($^i$PrMgCl solution) of 2M isopropyl magnesium chloride (0.35 equivalents, 11.2 ml) and hexane solution ($^n$BuLi solution) of 1.67M normal-butyl lithium (0.7 equivalents, 26.8 ml) were added dropwise. The mixture was stirred for 2 hours at −10° C. Then allyl bromide (1.1 equivalents, 6.8 ml) was added and stirred at room temperature for 14 hours. To the reacted mixture, diethyl ether was added and neutralized by adding saturated ammonium chloride. The obtained water layer was extracted by diethyl ether. The collected organic layer was washed with saturated saline solution, dried over anhydrous magnesium sulfate, then filtered and concentrated under reduced pressure, obtaining a crude product of 1-allyl-4-bromobenzene (2) (yield: 13.0 g, yield (%): 103%)

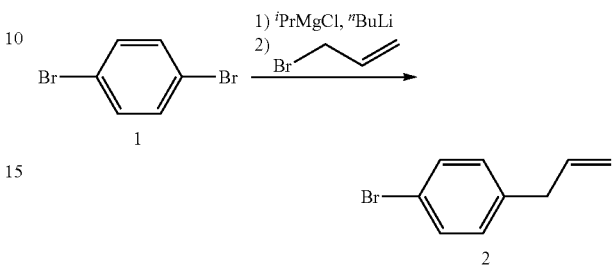

The physical and chemical analysis results of $^1$H-nuclear magnetic resonance spectroscopy ($^1$H NMR) of this crude product are showed below. $^1$H NMR (CDCl$_3$) δ=7.41 (d, J=8.0 Hz, 2H), 7.06 (d, J=8.0 Hz, 2H), 5.88-5.96 (m, 1H), 5.05-5.09 (m, 2H), 3.33 (d, J=6.8 Hz, 2H)

The physical and chemical analysis results support the chemical formula (2).

(1.2) Under a nitrogen atmosphere, to 1-allyl-4-bromobenzene (2) (13.2 g, 55.1 mmol) and (Bu$_4$N)$_2$[PtCl$_6$](50.0 mg, 0.1 mol %), distilled methylene chloride (25 ml) and distilled diethyl ether (25 ml) were added and cooled to 0° C. Trichlorosilane (2 equivalents, 11.1 ml) was added, stirred at a room temperature for 12 hours. Then, concentrated under reduced pressure, and cooled to 0° C. under a nitrogen atmosphere. Diethyl ether solution (CH$_2$=CH—CH$_2$—MgBr solution) of 1M allylmagnesium bromide (4 equivalent, 220.4 ml) was added dropwise then stirred at room temperature for 15 hours. Diethyl ether was added to the reacted mixture, then neutralized with saturated ammonium chloride aqueous solution. The obtained water layer was extracted with dimethyl ether. The collected organic layer was washed with saturated saline solution and dried over anhydrous magnesium sulfate, filtered and concentrated under reduced pressure, obtaining a crude product. The crude product was separated and purified using silica gel column chromatography (eluent: n-hexane). 4-{3-(triallylsilyl)propyl}phenyl bromide (3) is obtained which is represented by the following chemical formula (yield: 16.3 g, yield (%): 87%).

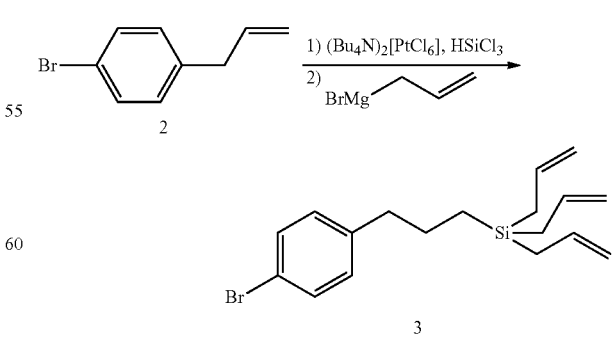

The physical and chemical analysis results of $^1$H NMR of this crude product are showed below.

$^1$H NMR (CDCl$_3$) δ=7.81 (d, J=8.0 Hz, 2H), 7.32 (d, J=8.0 Hz, 2H), 5.70-5.82 (m, 3H), 4.84-4.89 (m, 6H), 2.70 (t, J=3.4 Hz, 2H), 1.62-1.66 (m, 2H), 1.58 (d, J=7.6 Hz, 6H), 0.58-0.63 (m, 2H)

The physical and chemical analysis results support the chemical formula (3).

(1.3) Under a nitrogen atmosphere, to 4-{3-(triallylsilyl)propyl}phenyl bromide (3) (14.2 g, 40.6 mmol), tetrahydrofuran (THF) (50 ml) was added, cooled to −10° C. using salt ice. 2M of $^i$PrMgCl solution (0.70 equiv., 14.2 ml) and 1.67M of $^n$BuLi solution (1.4 equiv., 34.0 ml) were each added dropwise, then stirred at around −10° C. for 2 hours. N,N-dimethylformamide (DMF) (2 equiv., 6.3 ml) was added and stirred at room temperature for 14 hours. To the reacted mixture, diethyl ether was added and then neutralized with saturated ammonium chloride aqueous solution. The obtained water layer was extracted with diethyl ether, the collected organic layer was washed with saturated saline solution then dried over anhydrous magnesium sulfate, then filtered and concentrated under reduced pressure, obtaining a crude product. The crude product was separated and purified using silica gel column chromatography (eluent: hexane/ethyl acetate=20/1), obtaining 4-{3-(triallylsilyl)propyl}benzaldehyde (4) represented by the following chemical formula (yield: 11.0 g, yield (%): 89%).

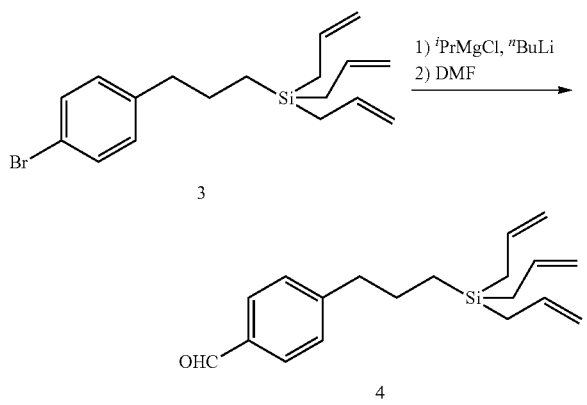

The physical and chemical analysis results of $^1$H NMR of this crude product are showed below.

$^1$H NMR (CDCl$_3$) δ=9.98 (s, 1H), 7.78 (d, J=6.8 Hz, 2H), 7.32 (d, J=7.2 Hz, 2H), 5.70-5.81 (m, 3H), 4.84-4.89 (m, 6H), 2.68 (t, J=3.6 Hz, 2H), 1.66-1.70 (m, 2H), 1.58 (d, J=7.6 Hz, 6H), 0.61-0.65 (m, 2H)

These physical and chemical analysis results support the chemical formula (4).

(1.4) Under a nitrogen atmosphere, tetramethoxysilane (5) (3.0 g, 19.7 mmol) was charged into a reaction container, cooled to 0° C., diethyl ether solution of 1M allylmagnesium bromide (78.8 ml, 78.8 mmol) was added dropwise. After the adding, stirring was continued at room temperature for 2 hours. The reacted mixture was diluted with water to stop the reaction, and 10% hydrochloric acid was added until salt was completely dissolved. The obtained organic layer was separated and the obtained water layer was extracted with diethyl ether. The collected organic layer was washed in this order with saturated sodium bicarbonate aqueous solution, saturated saline solution. After dried over anhydrous magnesium sulfate, filtered, concentrated under reduced pressure, obtaining triallylmethoxysilane (6) represented by the following chemical formula (yield: 3.59 g, yield (%): 100%).

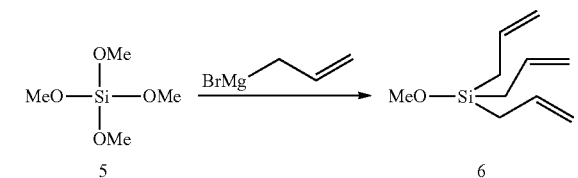

The physical and chemical analysis results of $^1$H NMR of this crude product are showed below.

$^1$H NMR (CDCl$_3$) δ=1.713 (d, J=8.4 Hz, 6H), 3.513 (s, 3H). 4.910-4.991 (m, 6H), 5.769-5.856 (m, 4H)

These physical and chemical analysis results support the chemical formula (6).

(1.5) Glass beads were pretreated by immersing then into concentrated nitric acid, then was ultrasonic treated for 15 minutes then washed with water. To these glass beads, sulfuric acid:hydrogen peroxide (7:3, Piranha solution) was added and left it overnight. After that, washed with water, dried in vacuum at 150° C., for 5 hours, obtaining surface activated glass beads (8).

(1.6) To triphenylphosphine dibromide (Ph$_3$PBr$_2$) (6.0 g, 0.9210 mmol), distilled dichloromethane (20.0 ml) was added under a nitrogen atmosphere and then dissolved. After that, a solution, in which triallylmethoxysilane (6) (2.8 mg, 0.8373 mmol) was added and dissolved into a distilled dichloromethane (15 ml) was added, and stirred at room temperature for 5 hours, to obtain halogenosilyl group containing compound (7). After stirring, the activated glass beads (8) which were treated by the Piranha solution were added, and stirred at room temperature for 4 hours. The reacted mixture was diluted with water to stop the reaction. Then 10% hydrochloric acid was added until the salt was completely dissolved. Then, filtered to take out the glass beads, washed three times each with toluene, ethanol, diethyl ether, and then dried, obtaining glass beads (9) on which triallylsilyl groups were attached as shown in the following chemical formula.

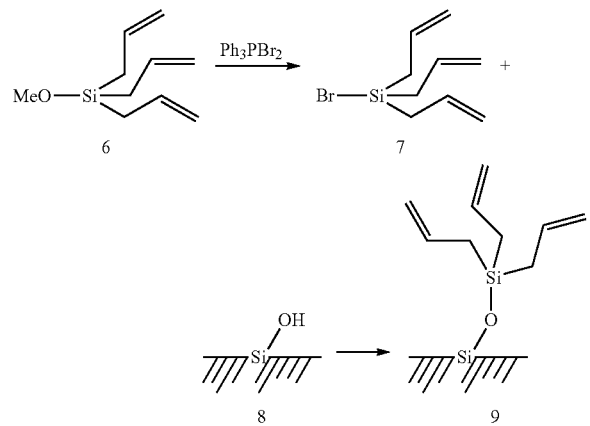

These physical and chemical analysis results of Fourier Transform-Infrared absorption spectrum (FT-IR) method of this product are showed below. In untreated glass beads, O—H stretching was seen around the 3500 cm$^{-1}$ but in the treated glass beads, C—H stretching induced from an allyl group was seen around 2850 cm$^{-1}$ and 2918 cm$^{-1}$. These physical and chemical analysis results support the chemical formula (9).

Instead of the glass beads previously described in (1.6), a slide glass which was cut into a shape of one side 2 cm×2 cm was surface-treated and physical and chemical analysis were carried out. As the surface activating treatment, untreated and various treatments such as pretreated cleaning, overnight dip treatment with Piranha solution, allylsilylation treatment, overnight dip treatment with alkaline solution (48 wt % aqueous solution of sodium hydroxide) and allylsilylation treatment were performed. Allylsilylation treatment was carried out in the same manner described in the glass beads treatment. Concerning the state of the slide glass surfaces, water contact angles were measured as physical and chemical analysis. Results of the water contact angles are showed in Table 1 together.

TABLE 1

Water Contact Angle on Glass Surface

| Method of Treatment | Water Contact Angle (°) |
|---|---|
| No-Treatment | 50.0 |
| Pretreated Cleaning (No-Allylsilyl Treatment) | 37.7 |
| Piranha Solution Treatment only (No-Allylsilyl Treatment) | 34.2 |
| Piranha Treatment and Allylsilyl Treatment | 67.7 |
| Alkaline Solution Treatment only (No-Allylsilyl Treatment) | 36.9 |
| Alkaline Solution Treatment and Allylsilyl Treatment | 70.5 |

As clearly seen from Table 1, once a slide glass surface is changed to hydrophilicity, the water contact angles tend to become larger when it receives an allylsilyl treatment. This means that the allylsilyl treatment makes the slide glass become hydrophobicity. These results indirectly support that the slide glass surfaces were allylsilylated by allylsilyl treatment.

(1.7) To 100 mg of glass beads (9) on which triallylsilyl group was attached, tetrahydrofuran (THF, 2 ml) and 2N hydrochloric acid (150 μl) were added and stirred for 30 minutes. Then 4-{3-(triallylsilyl)propyl}benzaldehyde (4) (100 mg) was added and stirred at room temperature for 13 hours. Glass beads were filtered out, washed three times each with distilled water, toluene, ethanol, diethyl ether and then dried. Silane coupling-reacted glass beads (10) via ether bonds were obtained.

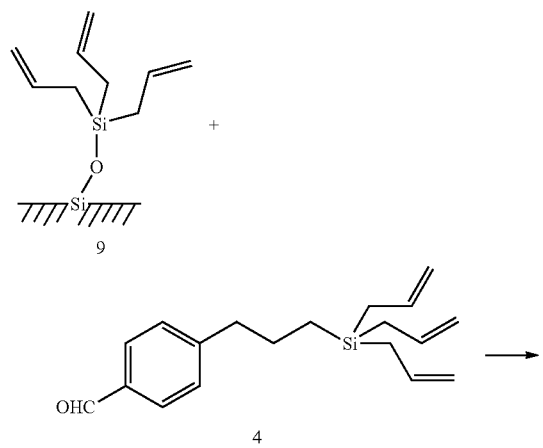

The physical and chemical analysis result of FT-IR of chemical formula (10) after 4-{3-(triallylsilyl)propyl}benzaldehyde (4) was supported is showed below. 4-{3-(triallylsilyl)propyl}benzaldehyde (4) supported glass beads had peaks based on C—H stretching at 2987 cm$^{-1}$, 2901 cm$^{-1}$ and peaks based on C=O stretching at 1716 cm$^{-1}$, 1684 cm$^{-1}$ were each confirmed. An increase in C=H stretching was also observed. These physical and chemical analysis results support the chemical formula (10).

(1.8) This chemical formula (10) can be used as a functional material. As described above, it was shown that alkoxysilane or allylsilane having any functional group can be functionalized under a sol-gel condition of hydrochloric acid. When materials that support an aldehyde group, for example, are mixed with amine, amine odor can be eliminated.

Example 2

(2.1) To triphenylphosphine dibromide (447.5 mg, 1.060 mmol), distilled dichloromethane (5 ml) was added under a nitrogen atmosphere and dissolved. Then a solution prepared by dissolving 1-bromo-4-(diallylethoxysilyl)benzene (11) (300 mg, 0.9637 mmol) into distilled dichloromethane (1.5 ml) was added and stirred at room temperature for 12 hours. After stirring, diethyl ether solution of 1M allylmagnesium bromide (1.156 ml, 1.156 mmol) was added dropwise and stirred at room temperature for 5 hours. The reacted mixture is cooled down to 0° C. and diluted with water to stop the reaction. 10% hydrochloric acid was added until salt was completely dissolved. The obtained organic layer was separated and the obtained water layer was extracted with dichloromethane. The collected organic layer was each washed with saturated sodium bicarbonate aqueous solution and saturated saline solution in this order, and dried over anhydrous magnesium sulfate and then filtered and concentrated under reduced pressure, obtaining a crude product. The crude product was passed through a silica gel short column (eluent: hexane/ethyl acetate=10/1), obtaining 1-bromo-4-(triallylsilyl)benzene (12) (yield: 256.4 mg, yield (%): 87%).

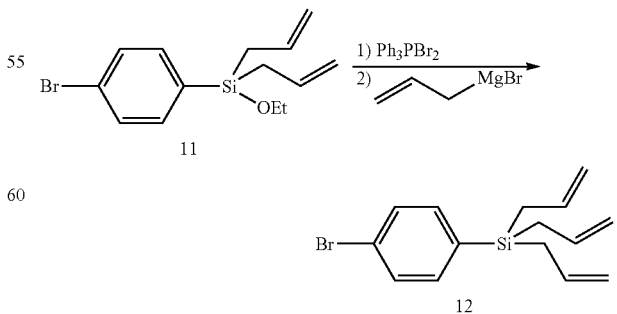

These physical and chemical analysis results according to $^1$H NMR are shown below.

$^1$H NMR (CDCl$_3$) δ=1.845 (d, J=8.4 Hz, 6H), 4.881-4.941 (m, 6H), 5.703-5.811 (m, 3H), 7.366 (d, J=8.4 Hz, 2H), 7.498 (d, J=10 Hz, 2H)

These physical and chemical analysis results support the chemical formula (12).

(2.2) Using this compound of the chemical formula (12), a functional material was prepared in the same manner as described above through silane coupling agent. If the silane coupling agent had a diallylethoxysilyl group, a small amount of ethanol was generated when the functional material was prepared through loading (or supporting) or performing a sol-gel reaction. On the other hand, as in this Example, when the functional material was prepared through loading (or supporting) or performing a sol-gel reaction using silane coupling agent having a triallylsilyl group, gaseous propene at room temperature was released from the reaction system and it was eliminated from the reaction system, therefore there was no alcohol remained in the system.

Example 3

(3.1) To triphenylphosphine dibromide (129.6 mg, 0.3070 mmol), distilled dichloromethane (2 ml) was added under a nitrogen atmosphere and dissolved. Then a solution prepared by dissolving 1-iodo-4-(diallylethoxysilyl)benzene (13) (100 mg, 0.2791 mmol) into a distilled dichloromethane (1 ml) was added, stirred at room temperature for 3 hours. After stirring, diethyl ether solution of 1M allylmagnesium bromide (0.6978 ml, 0.6978 mmol) was added dropwise, stirred at room temperature for 2 hours. The reacted mixture was cooled down to 0° C., then diluted with water to stop the reaction. 10% hydrochloric acid was added until all salt was completely dissolved. The obtained organic layer was separated and the obtained water layer was extracted with dichloromethane. The collected organic layer was each washed with saturated sodium bicarbonate aqueous solution and saturated saline solution in this order, then dried over anhydrous magnesium sulfate, then filtered and condensed under reduced atmosphere, obtaining a crude product. The crude product was passed through a silica gel short column (eluent: hexane/ethyl acetate=10/1). As is shown in the following chemical reaction equation, 1-iodo-4-(triallylsilyl)benzene (14) was obtained (yield: 81.4 mg, yield (%): 82%).

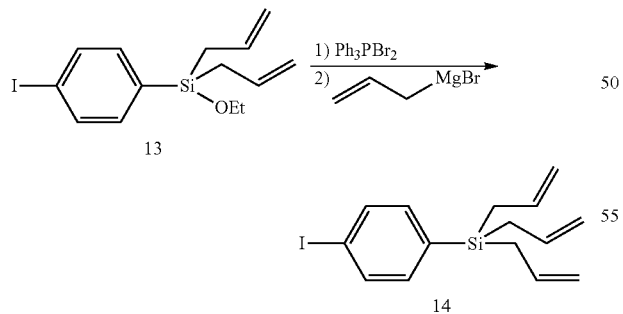

These physical and chemical analysis results according to $^1$H NMR are shown below.

$^1$H NMR (CDCl$_3$) δ=1.839 (d, J=8.4 Hz, 6H), 4.883-4.936 (m, 6H), 5.700-5.808 (m, 3H), 7.229 (d, J=7.6 Hz, 2H), 7.705 (d, J=8.4 Hz, 2H)

These physical and chemical analysis results support the chemical formula (14).

(3.2) Using this compound of the chemical formula (14), as in the same manner described above, a functional material can be prepared through a silane coupling agent.

Example 4

(4.1) Magnesium (flaked state) (50.89 mg, 2.093 mmol) was activated using a heat gun under reduced pressure (vacuum) for 30 minutes, then THF (0.2 ml) distilled under a nitrogen atmosphere was added, then a small amount of iodine was added. Stirring was continued at room temperature until the color of iodine was lost. To this, bromobenzene (15) (329.8 µL, 3.140 mmol) was dissolved into a distilled THF/distilled diethyl ether (0.4 ml/0.6 ml) and then the thus obtained solution was added dropwise. At this time, a reaction container thereof was cooled down with water, kept at room temperature. After the end of the dropwise adding, stirring was continued at room temperature for 4 hours.

(4.2) On the other hand, to triphenylphosphine dibromide (388.8 mg, 0.9210 mmol) distilled dichloromethane (5.5 ml) was added under a nitrogen atmosphere and dissolved. After that, a solution which was prepared by dissolving 1-iodo-4-(diallylethoxysilyl)benzene (300 mg, 0.8373 mmol) to distilled dichloromethane (1.3 ml) was added and stirred at room temperature for 7 hours. After the stirring, phenylmagnesium bromide (PhMgBr, 2.5 equiv.) was dropped, then stirred at room temperature for 14 hours. The reacted mixture was cooled down to 0° C. and diluted by water to stop the reaction. Then 10% hydrochloric acid was added until the salt is completely dissolved. The obtained organic layer was separated and the obtained water layer was extracted with dichloromethane. The collected organic layer was washed with each saturated sodium bicarbonate aqueous solution and saturated saline solution in this order, dried over anhydrous magnesium sulfate, filtered, and concentrated under reduced pressure, obtaining a crude product. The crude product was passed through a short column of silica gel (eluent: hexane/ethyl acetate=10/1), 1-iodo-4-(triallylphenylsilyl)benzene (17) represented by the following chemical formula was obtained (yield: 282.5 mg, yield (%): 86%).

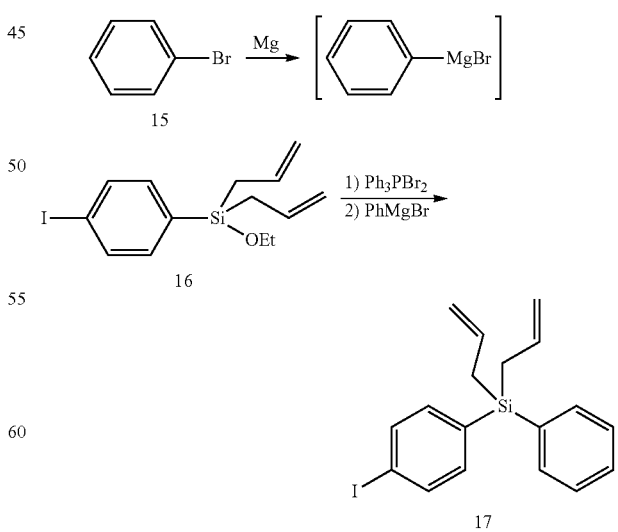

These physical and chemical analysis results according to $^1$H NMR are shown below.

$^1$H NMR (CDCl$_3$) δ=2.095 (d, J=7.6 Hz, 4H), 4.879-4.941 (m, 4H), 5.702-5.809 (m, 2H), 7.221 (d, J=8.0 Hz, 2H), 7.336-7.445 (m, 3H), 7.481 (d, J=7.8 Hz, 2H), 7.699 (d, J=8.0 Hz, 2H)

These physical and chemical analysis results support the chemical formula (17).

(4.3) By using this compound of chemical formula (17), a functional material can be prepared, by way of a silane coupling agent, in the same manner described above.

Example 5

(5.1) Under a nitrogen atmosphere, trimethoxymethylsilane (18) (1,000 μL, 7.011 mmol) was added to a reaction container, cooled down to 0° C., then diethyl ether solution of 1M allylmagnesium bromide (14.72 ml, 14.72 mmol) was added dropwise. After the end of dropping, stirring was continued at room temperature for 2 hours. The reacted mixture was cooled down to 0° C., then diluted with water to stop the reaction, 10% hydrochloric acid was added until the salt was completely dissolved. Organic layer was separated, water layer was extracted with diethyl ether, then the collected organic layer was each washed with saturated sodium bicarbonate aqueous solution and saturated saline solution in this order. Then dried over anhydrous magnesium sulfate, filtered and concentrated under reduced pressure, obtaining methyl (diallyl)silane (19) represented by the following chemical reaction equation (yield: 986.5 mg, yield (%): 90%).

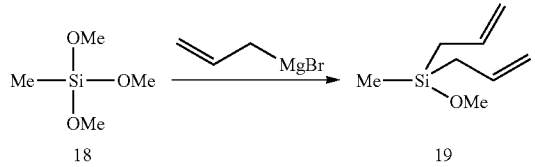

These physical and chemical analysis results according to $^1$H NMR are shown below.

$^1$H NMR (CDCl$_3$) δ=0.134 (s, 3H), 1.677 (d, J=8.0 Hz, 4H), 3.480 (s, 3H), 4.891-4.962 (m, 4H), 5.758-5.866 (m, 2H)

These physical and chemical analysis results support the chemical formula (19).

(5.2) By using this compound of chemical formula (19), a functional material can be prepared in the same manner described above through a silane coupling agent.

Conventionally, a compound having a diallylethoxysilyl group and diallylmethoxysilyl group have ethoxy group or methoxy group in its molecule, but they were only used for the sol-gel reaction induced from diallylsilyl group itself. As shown in the compound represented by chemical formula (17) and (19), these ethoxy group and methoxy group can be a clue of functional group transformation, being useful to induce silane coupling agents or functional materials.

Example 6

(6.1) Magnesium (flaked state) (116.7 mg, 4.798 mmol) was activated using a heat gun under reduced pressure (vacuum) for 30 minutes, then THF (0.46 ml) distilled under a nitrogen atmosphere was added, then a small amount of iodine was added. Stirring was continued at room temperature until the color of iodine was lost. To this, bromobenzene (755.9 μL, 7.198 mmol) was dissolved into a distilled THF/distilled diethylether (0.91 ml/1.37 ml) and then the thus obtained solution was added dropwise. At this time, a reaction container thereof was cooled down with water, kept at room temperature. After the end of the dropwise adding, stirring was continued at room temperature for 4 hours.

(6.2) On the other hand, to triphenylphosphine dibromide (891.2 mg, 2.111 mmol) distilled dichloromethane (12 ml) was added under a nitrogen atmosphere and dissolved. After that, a solution which was prepared by dissolving methyl (diallyl)methoxysilane (20) (300 mg, 1.919 mmol) to distilled dichloromethane (2.9 ml) was added and stirred at room temperature for 7 hours. After stirring, phenylmagnesium bromide (PhMgBr, 2.5 equiv.) was dropped, further stirred at room temperature for 14 hours. The reacted mixture was cooled down to 0° C., diluted with water to stop the reaction, 10% hydrochloric acid was added until the salt was completely dissolved. The obtained organic layer was separated and the obtained water layer was extracted with dichloromethane. The collected organic layer was washed each with saturated sodium bicarbonate aqueous solution and saturated saline solution in this order, then dried over anhydrous magnesium sulfate, then concentrated under reduced pressure, obtaining a crude product. The crude product was passed through a short column of silica gel (eluent: hexane/ethyl acetate=10/1). Diallyl(methyl)phenylsilane (21) represented by the following chemical equation below (yield: 282.5 mg, yield (%): 86%).

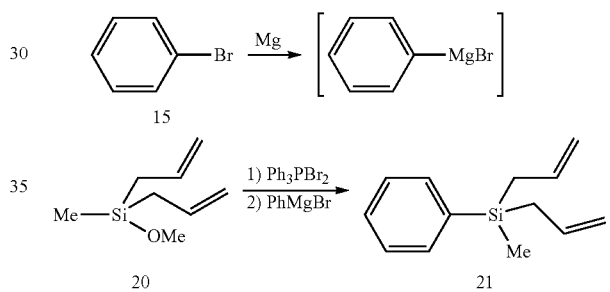

These physical and chemical analysis results according to $^1$H NMR are shown below.

$^1$H NMR (CDCl$_3$) δ=0.289 (s, 3H), 1.812 (d, J=8.2 Hz, 4H), 4.841-4.911 (m, 4H), 5.719-5.827 (m, 2H), 7.328 (m, 3H), 7.496-7.520 (m, 2H).

These physical and chemical analysis results support the chemical formula (21).

(6.3) Using the compound of chemical formula (21), in the similar manner described above, a functional material can be prepared by way of a silane coupling agent.

Example 7

A functional material was prepared in the same manner as described in Example 6, except that phenylmagnesium bromide in Example 6 was changed to bromo(phenyl)magnesium bromide. The functional material had similar functions as seen in Example 6.

Example 8

(8.1) Under a nitrogen atmosphere, (3-bromopropyl)trichlorosilane (22) (1 equiv., 5 g, 19.5 mmol) was cooled down to 0° C., then 1M allylmagnesium bromide solution (3.3 equiv., 64.5 ml) was added and stirred at room temperature for 3 hours. To the reacted mixture, diethyl ether was added and neutralized with aqueous solution of citric acid.

The obtained water layer was extracted with diethyl ether and the collected organic layer was washed with saturated saline solution, then dried over anhydrous magnesium sulfate and filtered, concentrated under reduced pressure, obtaining a crude product. The crude product was passed through silica gel column chromatography (eluent: n-hexane), obtaining triallyl(3-bromopropyl)silane (23) represented by the following chemical reaction equation (yield: 5.2 g, yield (%): 98%).

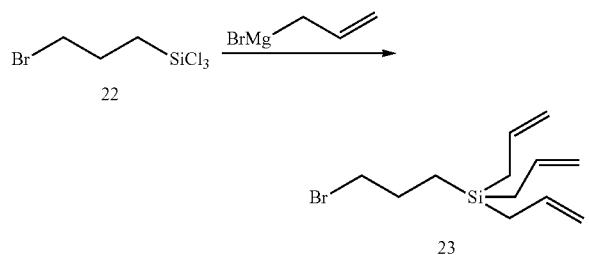

These physical and chemical analysis results according to $^1$H NMR are shown below.

$^1$H NMR (CDCl$_3$) δ=5.73-5.81 (m, 3H), 4.88-4.93 (m, 6H), 3.37 (t, J=7.2 Hz, 2H), 1.86-1.90 (m, 2H), 1.61 (d, J=8.4 Hz, 6H), 0.69-0.74 (m, 2H)

These physical and chemical analysis results support the chemical formula (23).

(8.2) Magnesium particles (flaked state) (934 mg, 38.4 mmol) were activated using a heat gun under reduced pressure (vacuum) for 30 minutes, then diethyl ether (5 ml) was added, then triallyl(3-bromopropyl)silane (23) (7.0 g, 25.2 mmol) dissolved in diethyl ether (20 ml) was slowly added dropwise and stirring was continued at room temperature for 13 hours. Diethyl ether solution of 3-(triallylsilyl)propylmagnesium bromide (24) represented by the following chemical reaction equation.

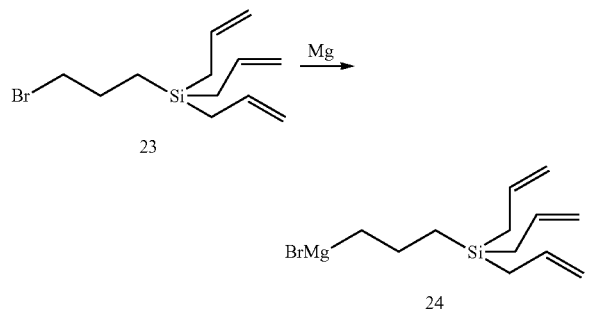

(8.3) The compound represented by the chemical formula (24) was reacted with, for example, trimethoxymethyl silane (18), in a similar manner described before, a functional material can be prepared by way of a silane coupling agent.

Example 9

(9.1) Under a nitrogen atmosphere, tert-butyl trichlorosilane (25) (10 g, 52.2 mmol) was added into a reaction container, then distilled diethyl ether was added and dissolved. Then completely cooled down to 0° C., distilled methanol (MeOH) (8.45 ml, 208.8 mmol) was added. Distilled triethylamine (NEt$_3$) (32 ml, 229.7 mmol) was added dropwise and stirred at room temperature for 1 hour. Then reacted mixture was filtered through Celite. Filtered solution was concentrated to obtain a crude product which was passed through a short column of silica gel (eluent: diethyl ether). Tert-butyl trimethoxysilane (26) represented by the following chemical reaction equation was obtained (yield: 9.02 g, yield (%): 97%).

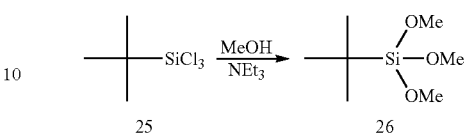

These physical and chemical analysis results according to $^1$H NMR are shown below.

$^1$H NMR (CDCl$_3$) δ=0.981 (s, 9H), 3.609 (s, 9H)

These physical and chemical analysis results support the chemical formula (26).

(9.2) Under a nitrogen atmosphere, tert-butyl trimethoxysilane (26) (1 g, 5.61 mmol) was added into a reaction container, cooled completely down to 0° C. 1M allylmagnesium bromide (28.1 ml, 28.1 mmol) was added dropwise under a nitrogen atmosphere and stirred at room temperature for 17 hours. After stirring, the reacted mixture was cooled to 0° C., diluted with diethyl ether and water was added to stop the reaction. Then 10% hydrochloric acid was added until the salt was dissolved. The obtained organic layer was separated and the obtained water layer was extracted with diethyl ether. The collected organic layer was washed each with saturated sodium bicarbonate aqueous solution, saturated saline solution in this order, then dried over anhydrous magnesium sulfate, filtered, concentrated under reduced pressure, obtaining a crude product. The crude product was distilled using Kugelrohr, obtaining tert-butyl diallyl methoxysilane (27) represented by the following chemical reaction equation (yield: 513.3 mg, yield (%): 46%).

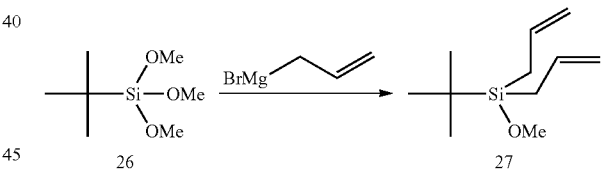

These physical and chemical analysis results according to $^1$H NMR are shown below.

$^1$H NMR (CDCl$_3$) δ=0.96 (s, 9H), 1.69-1.80 (m, 4H), 3.550 (s, 3H), 4.89-5.02 (m, 4H), 5.84-5.95 (m, 2H)

These physical and chemical analysis results support the chemical formula (27).

(9.3) Under a nitrogen atmosphere, to triphenylphosphine dibromide (234.1 mg, 0.555 mmol), distilled dichloromethane (4 ml) was added and dissolved. Then, a solution of tert-butyl diallyl methoxysilane (27) (100 mg, 0.504 mmol) dissolved in distilled dichloromethane (1.5 ml) was added and stirred at room temperature for 13 hours. After stirring, it was cooled down completely to 0° C., then distilled triethylamine (NEt$_3$) (0.085 ml, 0.605 mmol) was added dropwise, and 1-butanol (n-BuOH) (0.055 ml, 0.605 mmol) was added dropwise and stirred at room temperature for further 5 hours. The reacted mixture was cooled down to 0° C. and water was added to stop the reaction. Then 10% hydrochloric acid was added. The obtained organic layer was separated and the obtained water layer is extracted with dicyclomethane. The collected organic layer was watched each with saturated sodium bicarbonate aqueous solution and saturated saline solution in this order, dried over anhydrous magnesium sulfate, filtered and then concentrated under reduced pressure, obtaining a crude product. The crude product was passed through a short column of silica gel (eluent: hexane/ethyl acetate=20/1), tert-butyl diallyl butoxysilane (28) represented by the following chemical reaction equation (yield: 111.0 mg, yield (%): 92%).

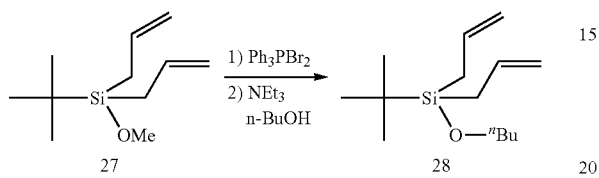

These physical and chemical analysis results according to $^1$H NMR are shown below.

$^1$H NMR (CDCl$_3$) δ=0.88 (t, J=6.8 Hz, 3H), 0.94 (s, 9H), 1.30-1.40 (m, 2H), 1.47-1.54 (m, 2H), 1.67-1.78 (m, 4H), 3.69 (t, J=6.4 Hz, 2H), 4.87-4.98 (m, 4H), 5.83-5.95 (m, 2H)

These physical and chemical analysis results support the chemical formula (28).

Example 10

(10.1) Tert-butyl trichlorosilane (25) (270 mg, 1.41 mmol) was dissolved in distilled THF, then 4.7 ml of diethyl ether solution of 0.9M 3-(triallylsilyl)propylmagnesium bromide (24) was added dropwise at 0° C., stirred at room temperature for 11 hours and then methanol and triethylamine were added and then stirred for 3 hours. To the reacted mixture, diethyl ether was added then neutralized with 1N hydrochloric acid. The obtained water layer was extracted with diethyl ether, and the collected organic layer was washed with saturated saline solution, dried over anhydrous magnesium sulfate, filtered and concentrated under reduced pressure, obtaining a crude product. The crude product was separated and purified using silica gel column chromatography (eluent: hexane/ethyl acetate=10/1), obtaining bis{3-(triallylsilyl)propyl}tert-butyl silanol (29) represented by the following chemical reaction equation (yield: 476 mg, yield (%): 69%).

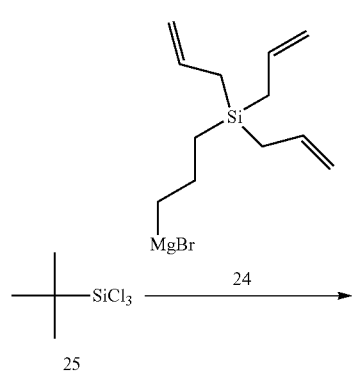

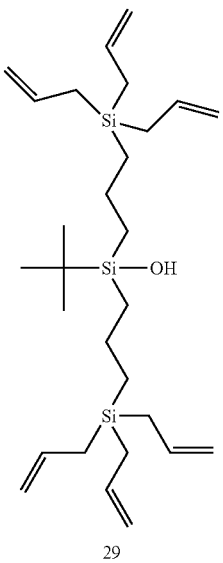

These physical and chemical analysis results according to $^1$H NMR are shown below.

$^1$H NMR (CDCl$_3$) δ=5.74-5.84 (m, 6H), 4.85-4.92 (m, 12H), 1.59 (d, J=8.4 Hz, 2H), 1.43-1.50 (m, 4H), 0.91 (s, 9H), 0.66-0.71 (m, 8H)

These physical and chemical analysis results support the chemical formula (29).

(10.2) Bis{3-(triallylsilyl)propyl}tert-butyl silanol (29) (10.3 mg, 0.02 mmol) was dissolved in distilled THF, two equivalents of Meerwein Reagent (Me$_3$OBF$_4$) and two equivalents of triethylamine were added dropwise and stirred at room temperature for 37 hours. To the reacted mixture, diethyl ether was added then 1N hydrochloric acid was added then the obtained water layer was extracted with diethyl ether. The collected organic layer was washed with saturated saline solution, dried over anhydrous magnesium sulfate, then filtered and concentrated under reduced pressure, obtaining bis{3-(triallylsilyl)propyl}(tert-butyl)methoxysilane (30) represented by the following chemical reaction equation (yield: 3.5 mg, yield (%): 33%).

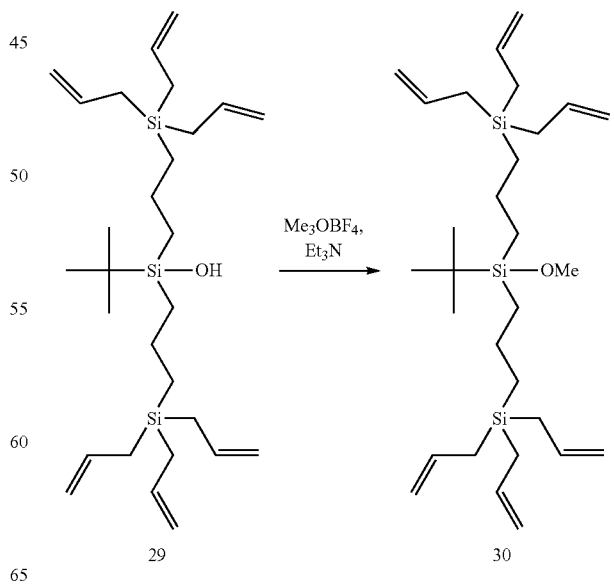

These physical and chemical analysis results according to $^1$H NMR are shown below.

$^1$H NMR (CDCl$_3$) δ=5.74-5.84 (m, 6H), 4.85-4.91 (m, 12H), 3.31 (s, 3H) 1.59 (d, J=8.4 Hz, 2H), 1.43-1.50 (m, 4H), 0.91 (s, 9H), 0.66-0.71 (m, 8H)

These physical and chemical analysis results support the chemical formula (30).

Example 10-1

Bis{3-(triallylsilyl)propyl}(tert-butyl)methoxysilane (30) can be simply synthesized in high yield using the following method.

(10-1.1) Under a nitrogen atmosphere, tetramethoxysilane (5) (0.482 ml, 3.268 mmol) was cooled down to 0° C., then diethyl ether solution of 10 ml (7.2 mmol) of 0.72M 3-(triallylsilyl)propylmagnesium bromide (24) was added dropwise, then stirred at room temperature for 15 hours. The reacted mixture was cooled down to 0° C., quenched with water, then saturated ammonium chloride aqueous solution was added until the salt was completely dissolved. The obtained organic layer was separated, and the obtained water layer was extracted with diethyl ether, the collected organic layer was each washed with saturated sodium bicarbonate aqueous solution and saturated saline solution in this order, dried over anhydrous magnesium sulfate, filtered, concentrated under reduced pressure, obtaining a crude product. The crude product was purified through short silica gel column chromatography (eluent: hexane/ethyl acetate=20/1), obtaining bis {(3-(triallylsilyl)propyl}dimethoxysilane (29') represented by the following chemical reaction equation (yield: 1.04 g, yield (%): 67%).

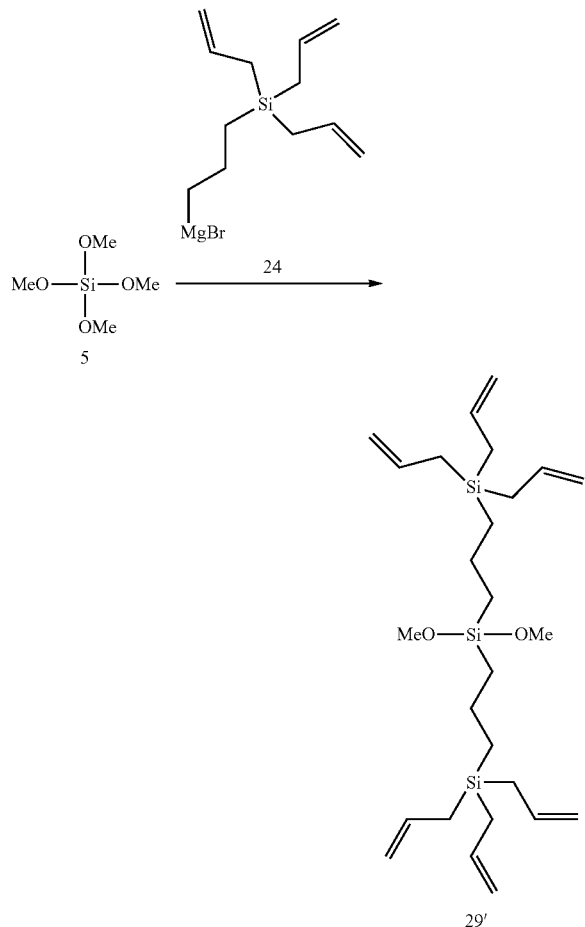

These physical and chemical analysis results according to $^1$H NMR are shown below.

$^1$H NMR (CDCl$_3$) δ=0.659-0.715 (m, 8H), 1.401-1.485 (m, 4H), 1.593 (d, J=8.2 Hz, 12H), 3.516 (s, 6H), 4.848-4.915 (m, 12H), 5.734-5.842 (m, 6H).

These physical and chemical analysis results support the chemical formula (29').

(10-1.2) Under a nitrogen atmosphere, bis{3-(triallylsilyl)propyl}dimethoxysilane (29') (1.0 g, 2.097 mmol) was cooled down to −78° C., then n-pentane solution of 1.61M t-butyllithium 1.954 mL (3.145 mmol) was added dropwise, then stirred at −78° C. for 17 hours. The reacted mixture was cooled down to 0° C., quenched with water, saturated ammonium chloride aqueous solution was added. The obtained organic layer was separated. The obtained water layer was extracted with diethyl ether and the collected organic layer was each washed with saturated sodium bicarbonate aqueous solution and saturated saline solution in this order, dried over anhydrous magnesium sulfate, filtered, concentrated under reduced pressure, obtaining a crude product. The crude product was purified through short silica gel column chromatography (eluent: hexane/ethyl acetate=20/1), obtaining bis({3-(triallylsilyl)propyl}(tert-butyl)methoxysilane (30) (yield: 0.902 g, yield (%): 85%).

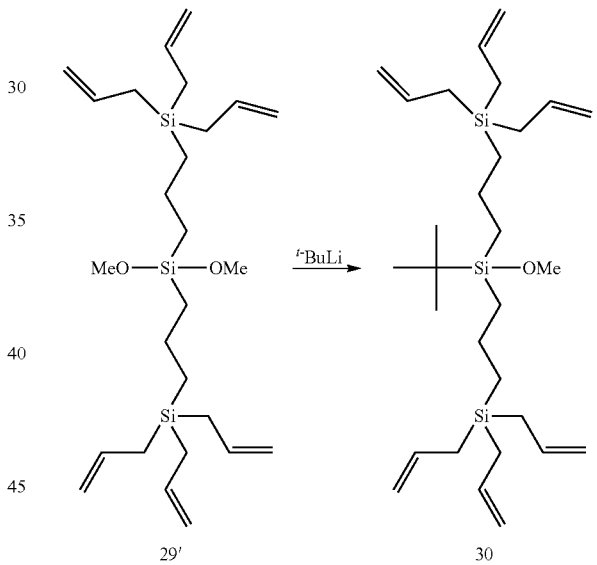

These physical and chemical analysis results according to $^1$H NMR are shown below.

$^1$H NMR (CDCl$_3$) δ=0.639-0.789 (m, 8H), 0.914 (s, 9H), 1.417-1.501 (m, 4H) 1.596 (d, J=8.4 Hz, 12H), 3.502 (s, 3H), 4.855-4.913 (m, 12H), 5.738-5.845 (m, 6H)

These physical and chemical analysis results support the chemical formula (30).

Example 11

(11.1) Under a nitrogen atmosphere, dimethoxydimethylsilane (31) (1.0 ml, 7.0 mmol) was added to a reaction container, cooled down to 0° C., diethyl ether solution of 0.72M 3-(triallylsilyl)propylmagnesium bromide (24) (19.44 mL, 14 mmol) was added dropwise. After the dropwise adding, stirring was continued at room temperature for 5 hours. To the reaction mixture, water was added to stop the reaction, then 10% hydrochloric acid was added until the salt was completely dissolved. The obtained organic layer was separated and the obtained water layer was extracted with diethyl ether. The collected organic layer was washed each with saturated sodium bicarbonate aqueous solution and saturated saline solution in this order, dried over anhydrous magnesium sulfate, then filtered, concentrated under reduced pressure, obtaining {3-(triallylsilyl)propyl}(methoxy)dimethylsilane (32) represented by the following chemical reaction equation (yield: 1.5 g, yield (%): 72%).

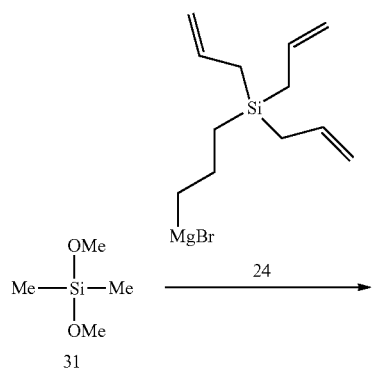

These physical and chemical analysis results according to $^1$H NMR are shown below.

$^1$H NMR (CDCl$_3$) δ=5.73-5.84 (m, 3H), 4.85-4.91 (m, 6H), 3.51 (s, 3H), 1.59 (d, J=7.6 Hz, 6H), 1.39-1.49 (m, 2H), 0.69-0.73 (m, 4H), 0.07 (s, 6H)

These physical and chemical analysis results support the chemical formula (32).

(11.2) Glass beads were immersed into concentrated nitric acid and treated by ultrasonic irradiation treatment for 15 minutes and then washed with water. To the treated glass beads, Piranha solution (sulfuric acid:hydrogen peroxide=7:3) was added and left it overnight. Then, they were washed with water and dried in vacuum at 150° C. for 5 hours.

(11.3) To triphenylphosphine dibromide (2.3 g, 5.5 mmol), distilled dichloromethane (15 ml) was added under a nitrogen atmosphere, to dissolve. Then, a solution, in which {3-(triallylsilyl)propyl}(methoxy)dimethylsilane (32) (1.5 g, 5.0 mmol) is dissolved in distilled dichloromethane (5 ml), was added and stirred at room temperature for 5 hours to obtain {3-(triallylsilyl)propyl}(bromo)dimethylsilane (33). After stirring, glass beads which was treated with Piranha solution was added and stirred further at room temperature for 4 hours. Water was added to the reaction mixture to stop the reaction, then 10% hydrochloric acid was added until the salt was dissolved. After that, glass beads were filtered out and washed each three times with toluene, ethanol and diethyl ether, dried, obtaining a functional material (34) represented by the following chemical reaction equation.

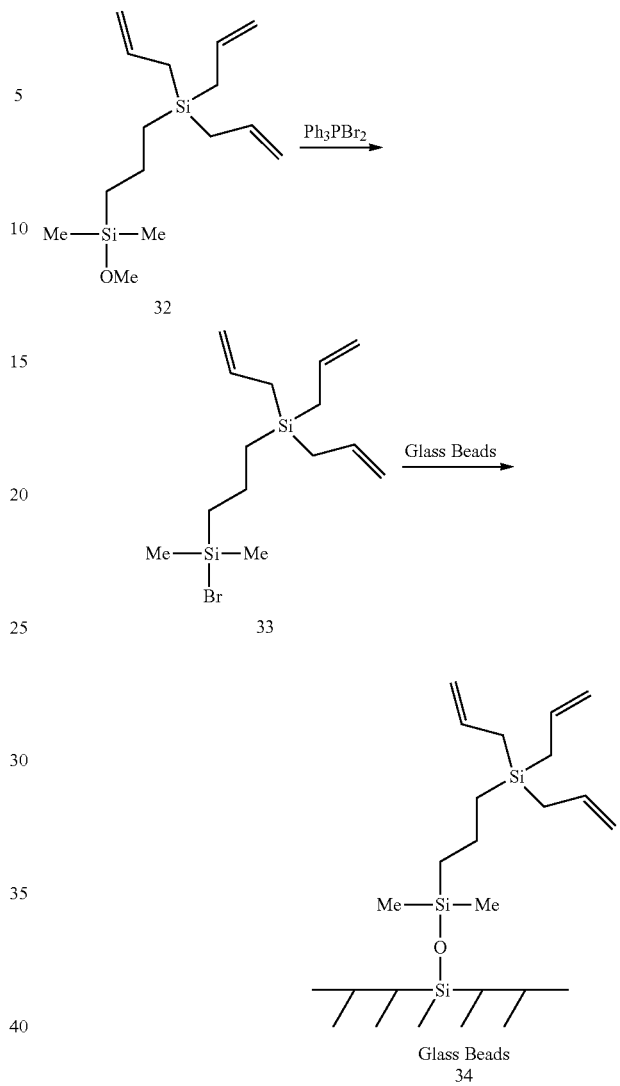

Example 12

Under a nitrogen atmosphere, trimethoxymethylsilane (18) (42 µl, 0.3 mmol) was added into a reaction container, cooled down to 0° C. and then diethyl ether solution of 0.9M 3-(triallylsilyl)propylmagnesium bromide (24) (1 mL, 0.9 mmol) was dropped. After dropping, stirring was continued at room temperature for 5 hours. To the reacted mixture, water was added to stop the reaction, then 10% hydrochloric acid was added until the salt was completely dissolved. The obtained organic layer was separated and the obtained water layer was extracted with diethyl ether. The collected organic layer was washed each with saturated sodium bicarbonate aqueous solution and saturated saline solution in this order, then dried over anhydrous magnesium sulfate, filtered, concentrated under reduced pressure, obtaining bis{3-(triallylsilyl)propyl}(methoxy)methylsilane (35) represented by the following chemical reaction equation (yield: 85 mg, yield (%): 62%).

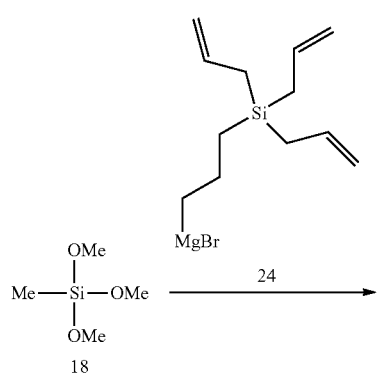

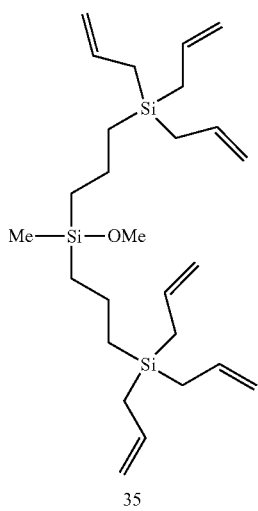

These physical and chemical analysis results according to $^1$H NMR are shown below.

$^1$H NMR (CDCl$_3$) δ=5.73-5.84 (m, 6H), 4.85-4.91 (m, 12H), 3.42 (s, 3H), 1.60 (d, J=7.6 Hz, 12H), 1.37-1.45 (m, 4H), 0.63-0.69 (m, 8H), 0.07 (s, 3H)

These physical and chemical analysis results support the chemical formula (35).

Example 13

By using (meth)allylsilane compound obtained in Example 12, a glass piece was treated in the similar way as described in Example 1, to perform allylsilylation of the glass surface. Similar contact angle results are shown in the surface contact angles as shown in Table 1. The allylsilylized glass pieces are immersed for 1 minute in 0.2 weight % solution in which octadecyl triallylsilane (36) and monoethoxy diallyl-1H, 1H, 2H, 2H-tridecafluoro-n-octylsilane (37) were diluted with hexane, and then heat treated at 150° C. for 30 minutes to complete a secondary processing. As shown in Example 1, glass surface water contact angles at their glass processing surface were measured. In addition, durability test was performed in which the glass processing surfaces were rubbed with steel wool No. 0000, 1 kg load and 100 reciprocations. After the reciprocating rubbing tests, their contact angles were measured. If there was no difference in contact angles between before and after the rubbing tests, they were rated "excellent". If the contact angles were lowered, it was rated "poor". "RUBBING TESTER" (Trade name, produced by Imoto machinery Co., LTD) was used for evaluating rubbing performance. The results are shown together in Table 2.

TABLE 2

| Treatment | Glass Surface Water Contact Angle (°) | | | |
|---|---|---|---|---|
| | Blank 1 | Example 13-1 | Blank 2 | Example 13-2 |
| No Treatment | 50.0 | 50.0 | 50.0 | 50.0 |
| Alkaline Treatment | 36.9 | 36.9 | 36.9 | 36.9 |
| Allylsilylation Treatment after Alkaline Treatment | — | 82.4 | — | 82.4 |
| Alkaline Treatment after Allylsilylation Treatment | — | 15.5 | — | 15.5 |
| Secondary Treatment (Octadecyl triallylsilane Treatment) | 100 | 100 | — | — |
| Secondary Treatment (Monoethoxy diallyl-1H,1H,2H,2H-tridecafluoro-n-octyl silane) | — | — | 92.5 | 92.5 |
| after Durability Test | 78 | 100 | 56.0 | 93.3 |
| Rating of Durability Test | poor | excellent | poor | excellent |

As clearly seen from Table 2, there are superior differences in durability according to allylsilylation of the glass surfaces. The results show that allylsilylation of the glass surfaces at the time of secondary treatment effectively gives durability to the surface function.

Example 14

(14.1) Under a nitrogen atmosphere, to 4-{3-(triallylsilyl)propyl}benzaldehyde (4) (11.0 g, 36.9 mmol), THF (25 ml) and methanol (MeOH) (25 ml) were added and then cooled down to at around 0° C. with ice, and then NaBH$_4$ (2.8 g, 73.8 mmol) was added and stirred for 3 hours. To the reacted mixture, saturated sodium bicarbonate aqueous solution was added. The obtained water layer was extracted with diethyl ether. The collected organic layer was washed with saturated saline solution, dried over anhydrous magnesium sulfate, filtered and concentrated under reduced pressure, obtaining a crude product. The crude product was separated and purified using silica gel column chromatography (eluent: n-hexane/ethyl acetate=5/1), obtaining 4-{3-(triallylsilyl)propyl}benzyl alcohol (38) represented by the following chemical reaction equation (yield: 9.2 g, yield (%): 84%).

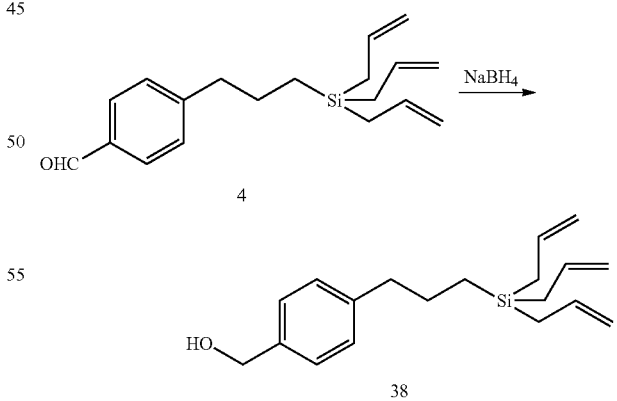

These physical and chemical analysis results according to $^1$H NMR are shown below.

$^1$H NMR (CDCl$_3$) δ=7.29 (d, J=7.6 Hz, 2H), 7.16 (d, J=8.0 Hz, 2H), 5.72-5.80 (m, 3H), 4.84-4.89 (m, 6H), 4.67 (d, J=4.4 Hz, 2H), 2.61 (t, J=7.4 Hz, 2H), 1.60-1.68 (m, 2H), 1.58 (d, J=7.6 Hz, 6H), 0.62-0.66 (m, 2H)

These physical and chemical analysis results support the chemical formula (38).

(14.2) Under a nitrogen atmosphere, 4-{3-(triallylsilyl)propyl}benzyl alcohol (5) (1.5 g, 5.0 mmol) and diethyl ether (15 ml) were charged into a reaction container and cooled down to −20° C., and then triphosgene (39) (1.48 g, 5.0 mmol) was added dropwise. And pyridine (40.2 μl, 0.50 ml) was added dropwise. After the end of dropwise adding, stirring was continued at room temperature for 2 hours. The reacted mixture was filtered with Celite. The filtrate was concentrated under reduced pressure, obtaining an acid chloride (40) represented by the following chemical equation (yield: 1.7 g, yield (%): 96%).

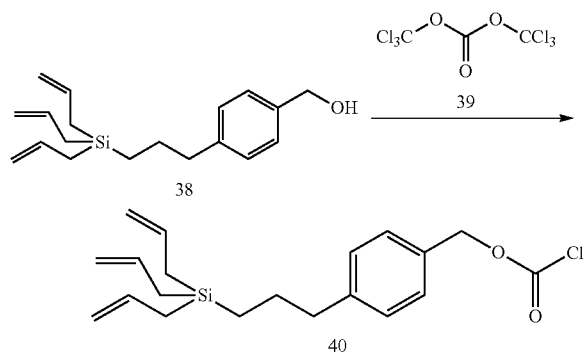

These physical and chemical analysis results according to $^1$H NMR are shown below.

$^1$H NMR (CDCl$_3$) δ 7.32 (d, J=7.6 Hz, 2H), 7.17 (d, J=8.0 Hz, 2H), 5.76 (m, 3H), 5.27 (s, 2H), 4.86 (m, 6H), 2.63 (t, J=7.4 Hz, 2H), 1.65 (m, 2H), 1.58 (d, J=7.6 Hz, 6H) 0.63 (m, 2H)

These physical and chemical analysis results support the chemical formula (40).

(14.2) Under a nitrogen atmosphere, benzylamine (41) (40 μl, 0.37 mmol) and THF (3 ml) were added to a reaction container, then cooled down to 0° C. Triethylamine (156 μl, 1.12 mmol) and acid chloride (40) (135.5 mg, 0.37 mmol) were added dropwise. After dropwise adding, stirring was continued at 0° C. for 1 hour, then at room temperature for 1 hour. To the reacted mixture, 3N diluted hydrochloric acid was added to make the reacted mixture acidified. Then the obtained organic layer was separated and the obtained water layer was extracted with diethyl ether. The collected organic layer was washed with saturated saline solution, dried over anhydrous sodium sulfate, filtered and, concentrated under reduced pressure, obtaining allylsilane compound (42), which is included in the present invention and represented by the following chemical reaction equation (yield: 155 mg, yield (%): 97%).

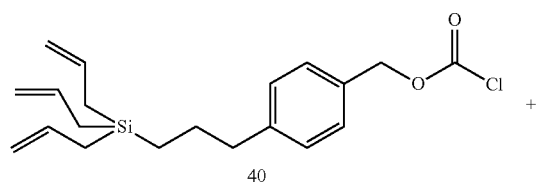

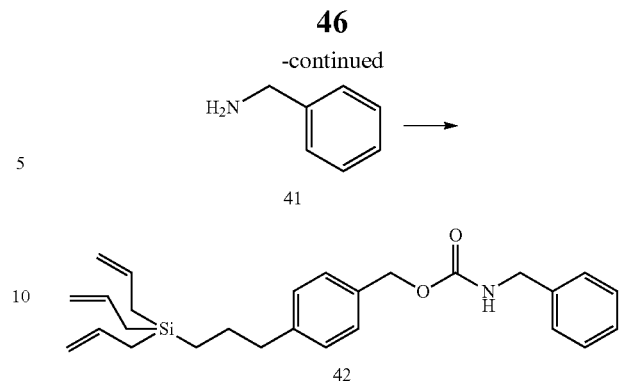

These physical and chemical analysis results according to $^1$H NMR are shown below.

$^1$H NMR (CDCl$_3$) δ 7.27-7.35 (m, 7H), 7.15 (d, J=8.0 Hz, 2H), 5.76 (m, 3H), 5.11 (s, 2H), 4.86 (m, 6H), 4.39 (d, J=5.6 Hz, 2H), 2.61 (t, J=7.4 Hz, 2H), 1.65 (m, 2H), 1.58 (d, J=7.6 Hz, 6H), 0.63 (m, 2H)

These physical and chemical analysis results support the chemical formula (42).

(14.3) Allylsilane compound represented by chemical formula (42) is attached to a glass piece and used as an antifogging material or attached to a chromatography carrier substrate such as a silica gel or resin powder and used as a functional material for column chromatography carriers.

Example 15

(15.1) Under a nitrogen atmosphere, threonine (43) (50 mg, 0.42 mmol) and NaHCO$_3$ (88.2 mg, 1.05 mmol) and THF (3 ml) were added into a reaction container, then cooled down to 0° C. Acid chloride (40) (152 mg, 0.42 mmol) dissolved in THF (0.5 ml) was added dropwise. After the end of dropwise adding, stirring was continued at 0° C. for 1 hour, then at room temperature, stirring was continued for another 1 hour. To the reacted mixture, 3N dilute hydrochloric acid was added to change it into the state of acidity. Then the obtained organic layer was separated, and the obtained water layer was extracted with diethyl ether. The collected organic layer was washed with saturated saline solution and then dried over anhydrous sodium sulfate, filtered, concentrated under reduced pressure, obtaining an allylsilane compound (44), which is included in the present invention, represented by the following chemical reaction equation.

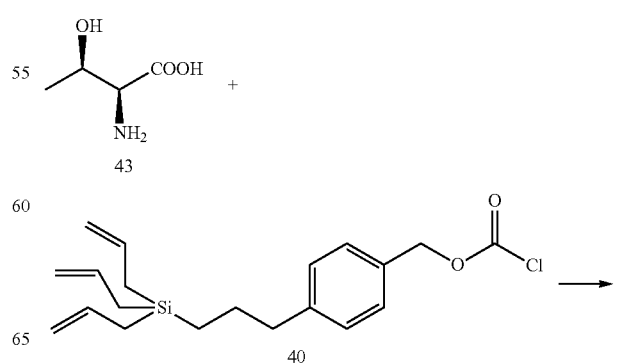

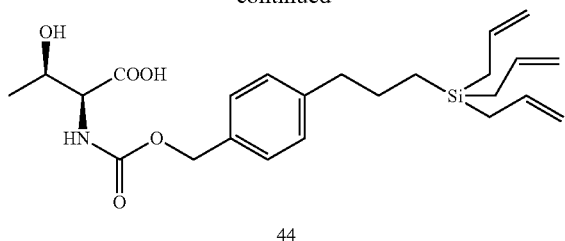

44

These physical and chemical analysis results according to $^1$H NMR are shown below.

$^1$H NMR (CDCl$_3$) δ 7.30 (d, J=7.6 Hz, 2H), 7.13 (d, J=8.0 Hz, 2H), 5.75 (m, 3H), 5.05 (m, 2H), 4.86 (m, 6H), 4.63 (s, 1H), 4.36 (m, 1H), 2.58 (m, 2H), 1.65 (m, 2H) 1.57 (d, J=8.4 Hz, 6H), 0.63 (m, 2H)

These physical and chemical analysis results support the chemical formula (44).

(15.2) The allylsilane compound of chemical formula (44) is used as functional materials such as anti-fogging material by attaching them to glasses or is used as an asymmetric identifiable column chromatography carrier by attaching them to a silica gel or resin powder.

Preparation Example 1

Preparation of Grignard Reagent

Under a nitrogen atmosphere, to 3-bromopropyltrichlorosilane (45) (5 g, 19.5 mmol) which was cooled down to 0° C., diethyl ether solution of 1M allylmagnesium bromide (3.3 equiv., 64.5 ml) was added and stirred for 3 hours at room temperature. To the reacted mixture, diethyl ether was added and neutralized with citric acid. The obtained water layer was extracted with diethyl ether. The collected organic layer was washed with saturated saline solution, dried over anhydrous magnesium sulfate, filtered and concentrated under reduced pressure, obtaining a crude product. The crude product was separated from undissolved components and purified, obtaining triallylsilyl propylbromide (46) represented by the following chemical reaction equation (yield: 5.2 g, yield (%): 98%).

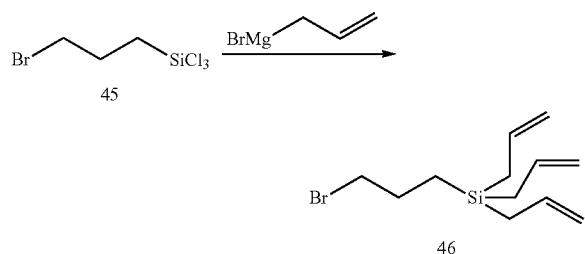

These physical and chemical analysis results according to $^1$H NMR are shown below. Here, any NMR spectrum were measured using JEOL ECX-400 (Trade name: produced by JEOL Ltd., 400 MHz for $^1$H NMR measurement, 376 MHz for $^{19}$F NMR measurement). As an internal standard, tetramethylsilane was used and displayed by ppm.

$^1$H NMR (CDCl$_3$) δ=5.73-5.81 (m, 3H), 4.88-4.93 (m, 6H), 3.37 (t, J=7.2 Hz, 2H), 1.86-1.90 (m, 2H), 1.61 (d, J=8.4 Hz, 6H), 0.69-0.74 (m, 2H)

These physical and chemical analysis results support the chemical formula (46).

Next, under a nitrogen atmosphere, to magnesium (934 mg, 38.4 mmol) which was activated by 1,2-dibromoethane, diethyl ether (5 ml) was added. Triallylsilyl propylbromide (46) (7.0 g, 25.2 mmol) dissolved in diethyl ether (20 ml) was slowly added dropwise and stirred at room temperature for 13 hours, preparing triallylsilylpropylmagnesium bromide (47), which was a Grignard reagent, represented by the following chemical reaction equation. Then, the concentration of the Grignard reagent was measured by acid-base titration using 1 mol/l hydrochloric acid and 1 mol/l sodium hydroxide solution. The result was 0.78M.

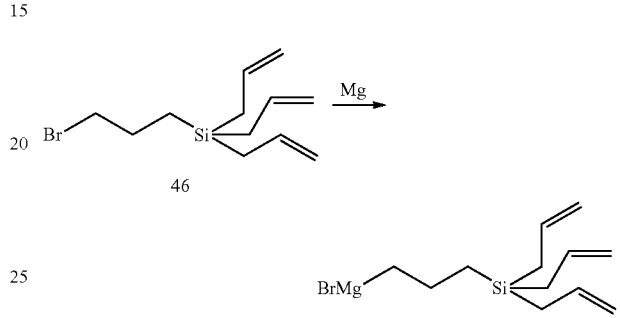

Example 16

Preparation of Perfluoro Group-Containing Allylsilane Compound <1>

(16.1; Reaction Between Fluorine Epoxy Compound (E-1630) and Triallylsilylpropylmagnesium Bromide)

Under a nitrogen atmosphere, to a 30 ml three-necked flask with a dropping funnel and a condenser tube, (E-1630 (1.0 g, 2.66 mmol, Trade name produced by DAIKIN INDUSTRIES. LTD) which was 3-perfluorohexyl-1,2-epoxypropane (48), copper iodide (50.6 mg, 2.66 mmol) and 3 ml of dehydrated diethyl ether (anhydrous Et$_2$O) were added and mixed. Next, 3.75 ml of 0.78M triallylsilylpropylmagnesium bromide (47) (diethyl ether solution) was added dropwise under an ice bath for 1 hour, after the end of dropwise adding, chemical reaction was made at room temperature for 5 hours, obtaining a reaction mixture of an alcohol intermediates (49) in which triallylsilylpropylmagnesium bromide was ring-openingly added to 3-perfluorohexyl-1,2-epoxypropane. To this reaction mixture, saturated ammonium chloride aqueous solution was added to stop the reaction. The obtained water layer was extracted with diethyl ether. The collected organic layer was washed with saturated sodium bicarbonate aqueous solution and saturated saline solution, the water layer and the organic layer were separated from each other. Then, the only organic layer was collected, dried over anhydrous magnesium sulfate, filtered, concentrated under reduced pressure, obtaining a crude product 2.25 g of a yellow transparent liquid. The obtained crude product, which was purified using silica gel chromatography (eluent: ethyl acetate), obtaining an alcohol intermediate as yellow liquid (49) represented by the following chemical reaction equation (yield: 1.49 g, yield (%): 96.3%).

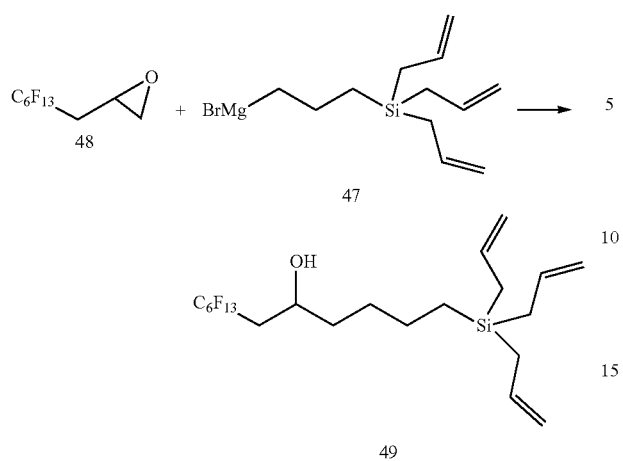

These physical and chemical analysis results according to $^1$H NMR and $^{19}$F are shown below.

$^1$H NMR (CDCl$_3$) δ=5.73-5.82 (m, 3H), 4.84-4.91 (m, 6H), 4.16 (m, 1H), 1.90 (m, 2H), 1.58-1.63 (m, 6H), 1.58 (d, J=7.6 Hz, 6H), 0.58-0.63 (m, 2H)

$^{19}$F NMR (CDCl$_3$) δ=−112.38, −121.81, −126.21

These physical and chemical analysis results support the chemical formula (49).

(16.2; Reaction Between Alcohol Intermediate and Acrylic Anhydride)

Under a nitrogen atmosphere, 0.33 g of acrylic anhydride, 0.35 g of triethylamine and 5 ml of toluene were added to 1.0 g of the alcohol intermediate (49) which was obtained in described above Example 1 (1.1), then they were reacted under refluxing for 8 hours. Progress of the reaction was checked using a thin-layer chromatography. After the end of the reaction, the reacted mixture was filtered and concentrated under reduced pressure, obtaining an ester body which was a crude product of perfluoro group-containing allylsilane compound as a brown viscous liquid represented by the following chemical reaction equation (yield: 0.84 g, yield (%): 76.9%).

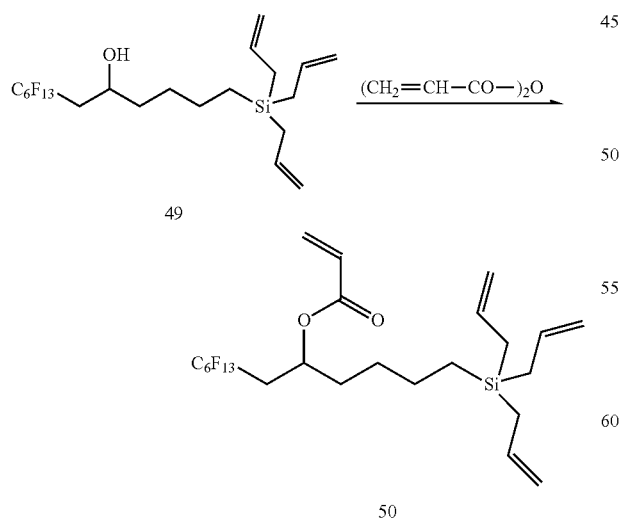

These physical and chemical analysis results according to $^1$H NMR and $^{19}$F NMR are shown below.

$^1$H NMR (CDCl$_3$): δ=6.45-6.40 (m, 1H), 6.15-6.05 (m, 1H), 5.90-5.81 (m, 1H), 5.73-5.82 (m, 3H), 4.84-4.91 (m, 6H), 4.16 (m, 1H), 1.90 (m, 2H), 1.58-1.63 (m, 6H), 1.58 (d, J=7.6 Hz, 6H), 0.58-0.63 (m, 2H)

$^{19}$F NMR (CDCl$_3$): δ=−126.21, −121.81, −112.38

These physical and chemical analysis results support the chemical formula (50).

Example 17

Preparation of Perfluoro Group-Containing Allylsilane Compound <2>

(17.1; Reaction Between Hexafluoropropene Trimer and Triallylsilylpropylmagnesium Bromide)

Under a nitrogen atmosphere, to a 30 ml three-necked flask with a dropping funnel and a condenser tube, 2.5 g of HFP (Trimer) (Trade name: produced by SIGMA-ALDRICH Co.) which was a hexafluoropropene trimer (51) and 5 ml of dehydrated THF were added and mixed.) Next, to this reacted mixture, 8.5 ml of 0.78M triallylsilylpropylmagnesium bromide (47) (diethyl ether solution) was added dropwise under an ice bath for 1 hour. After the end of dropwise adding, reaction was carried out at room temperature for 5 hours, obtaining a reaction mixture of additional intermediate (52) through nucleophilic reaction between hexafluoropropene trimer and triallylsilylpropylmagnesium bromide. To this reaction mixture, saturated ammonium chloride aqueous solution was added to stop the reaction, and the obtained water layer was extracted with diethyl ether. The collected organic layer was washed with saturated sodium bicarbonate aqueous solution and saturated saline solution to separate the water layer and the organic layer. After that, the only organic layer was collected and dried with anhydrous magnesium sulfate, filtered, concentrated under reduced pressure, obtaining a perfluoro group-containing allylsilane compound (52) represented by the following chemical reaction equation, the crude product having a yellow transparent liquid (yield: 2.64 g, yield (%): 76%).

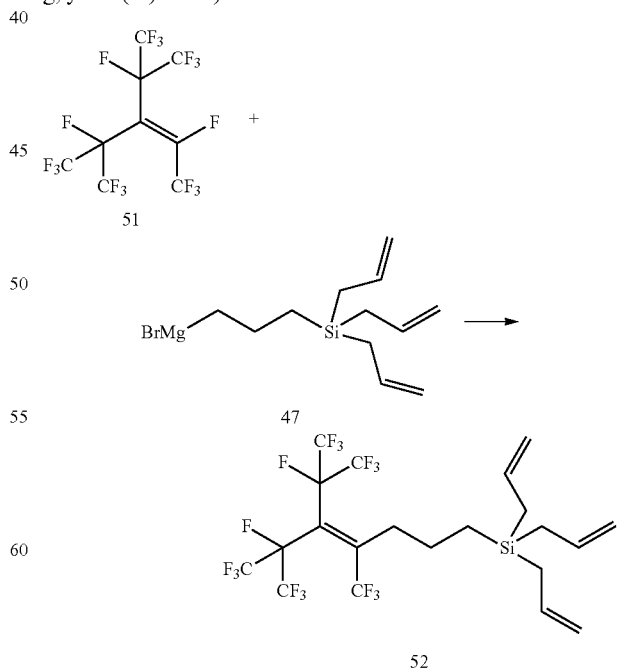

These physical and chemical analysis results according to $^1$H NMR and $^{19}$F NMR are shown below.

$^1$H NMR (CDCl$_3$) δ=5.73-5.81 (m, 3H), 4.88-4.93 (m, 6H), 1.61-1.59 (m, 10H), 0.59-0.61 (m, 2H)

$^{19}$F NMR (CDCl$_3$) δ=−111.82, −108.96, −99.41, −93.69, −81.70, −80.02, −75.65, −71.09, −66.80, −58.07

These physical and chemical analysis results support the chemical formula (52).

Preparation Example 2

Preparation of Grignard Reagent

Under a nitrogen atmosphere, to 1,2-dibromoethane activated magnesium (885 mg, 24.3 mmol), 3 ml of diethyl ether was added, 20 ml of diethyl ether which contains diallylsilylmethylpropyl bromide (6 g, 24.3 mmol) was slowly added dropwise and then stirring was continued at room temperature for 12 hours, preparing diallylsilylmethylpropyl magnesium bromide (53), a Grignard reagent. After that, the concentration of this Grignard reagent was measured using acid/base titration with 1 mol/l of hydrochloric acid and sodium hydroxide solution. The result was 0.75M.

Example 18

Preparation of Perfluoro Group-Containing Allylsilane Compound<3>

(18.1 Reaction Between Hexafluoropropene Trimer and Diallylsilylmethylpropyl Magnesium Bromide)

Under a nitrogen atmosphere, to a 30 ml three-necked flask with a dropping funnel and a cooling tube, 2.5 g of HFP (Trimer), a fluoropropene trimer (51), (Trade name: produced by SIGMA-ALDRICH Co.) and 5 ml of dehydrated THF was added and mixed. Next, 9.0 ml of 0.75M of methyldiallylsilylpropylmagnesium bromide (53) (diethyl ether solution) was added dropwise under an ice bath for 1 hour. After the end of dropwise adding, reaction was continued at room temperature for 5 hours, obtaining a reaction mixture of nucleophilic-reacted adduct (54) between hexafluoropropene trimer and methyldiallylsilylpropyl magnesium bromide. To this reaction mixture, saturated ammonium chloride aqueous solution was added to stop the reaction and the obtained water layer was extracted with diethyl ether. The collected organic layer was washed with saturate sodium bicarbonate aqueous solution and saturated saline solution, the water layer and the organic layer were separated. Then, the only organic layer was collected, dried over anhydrous magnesium sulfate, filtered, concentrated under reduced pressure, obtaining a crude product of perfluoro group-containing allylsilane compound (54) having a yellow transparent liquid represented by the following chemical reaction equation (yield: 2.52 g, yield (%): 76%).

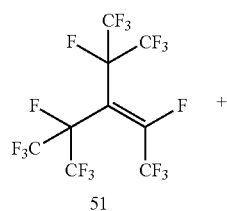

51

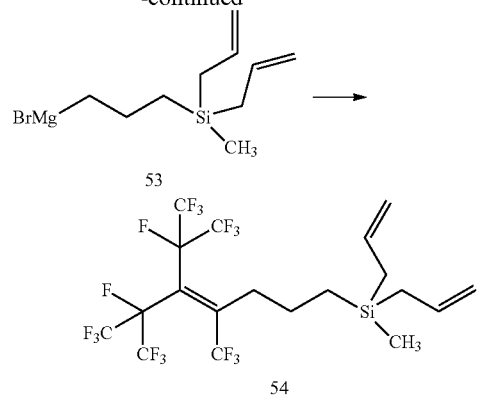

These physical and chemical analysis results according to $^1$H NMR and $^{19}$F NMR are shown below.

$^1$H NMR (CDCl$_3$) δ=5.73-5.81 (m, 2H), 4.88-4.93 (m, 4H), 1.61-1.59 (m, 8H), 0.59-0.61 (m, 2H), 0.08-0.00 (s, 3H)

$^{19}$F NMR (CDCl$_3$) δ=−111.82, −108.96, −99.41, −93.69, −81.70, −80.02, −75.65, −71.09, −66.80, −58.07

These physical and chemical analysis results support the chemical formula (54).

Manufacturing Example 1

Preparation of Chemically Modified Colloidal Silica

To the particle surface of colloidal silica MIBK-ST (Trade name: produced by Nissan Chemical Industries, Ltd., particle diameter: 10 nm to nm, solid content: 30%), fluorine group was introduced for chemical modification as follows. 1 g of colloidal silica was suspended in 2 ml of methyl isobutyl ketone. 0.14 g of perfluoro group-containing allylsilane compound (54) prepared in Example 3 was added and heat treated at 80° C. As shown in the following chemical reaction, filler particles in which the perfluoro group-containing allylsilane compound was bonded to a surface of the colloidal silica particle was prepared.

Manufacturing Example 2

Preparation of Coating Composition

The suspending liquid obtained in the Manufacturing Example 1 and 0.7 g of a coating composition HX-400UV (Trade name: produced by kyoeisha Chemical Co., Ltd.) were mixed and kneaded to prepare the coating composition.

Manufacturing Example 3

Preparation of Coating Material

The coating composition obtained in the Manufacturing Example 2 was coated with a constant film thickness on a base material, a polyethylene terephthalate (PET) film A4300 (Trade name: produced by TOYOBO CO., LTD. film thickness: 125 nm) and then an urethane acrylate was cured by using a UV irradiation machine, CV-1100-G (Trade name: produced by Heraeus Noblelight Fusion UV K.K.). More specifically, curing was carried out at 60° C., 5 minutes of predrying, and then ultraviolet irradiation was carried out at 600 mJ (200 mJ×3 passes) to obtain coating materials.

Comparative Manufacturing Example

Preparation of Coating Composition and Coating Material

Coating composition and coating material, which are outside the present invention, were prepared in the same manner as described in the Manufacturing Examples 1 to 3 except that un-treated colloidal silica was used instead of the chemically modified colloidal silica.

(Performance Evaluation)

(i) Concerning the appearance of coating composition: presence or absence of solid matter or insoluble matter was visually checked.
(ii) Concerning the appearance of the coated film when coating composition was coated was visually checked.
(iii) Concerning the physical properties of the coating film surface side of the coating material: presence or absence of interference fringe and haze were visually checked.
(iv) Concerning the hardness of the coating film surface side of the coating material: when the load was 500 g, a pencil hardness corresponding without scratch was evaluated according to the scratch hardness (pencil hardness: JIS K 5600-5-4).
(v) Concerning the anti-scratching property of the coating film surface side of the coating material: steel wool (No. 0000) applied load of 1 kg was reciprocated 10 times. The anti-scratch property was evaluated on a scale of "scratch" or "no-scratch" by visual contact.
(vi) Concerning the adhesiveness of the coating film surface side of the coating material: cross-cut test (JIS K5400) was carried out, in which the number of no-peeling squares were counted.
(vii) Concerning the curling test of the coating film surface side of the coating material: the coating materials were cut out in the size of 10 cm×cm square. Gap heights of the four edges were measured and averaged. The average value was less than 10 mm, then the coating materials were evaluated as no curling.
(viii) Concerning the contact angle of the coating film surface side of the coating material: the contact angles between water and the coating film surface side, between oleic acid and thereof were measured according to JIS R 1703.
(viii) Concerning a wiping off property of the coating film surface side of the coating material: presence or absence of printed fingerprints on the coated film were visually checked whether there was fingerprint attached on the coated film after the fingerprints were softly wiped out.
(ix) Concerning antifouling property of the coating film surface side of the coating material: the coating surface was drawn with permanent marker ink pen and then the marker ink was softly wiped out. The surface was visually observed whether there were remains of the ink. These results are shown together in Table 3.

TABLE 3

| Evaluation Item | | Preparative Example Filler (Chemically Modified Colloidal Silica) | Comp. Preparative Example Filler (non-modified) |
|---|---|---|---|
| Coating Composition | Appearance | Good | Good |
| Coated Layer of Coating Material | Thickness of Coated Layer (μm) | 5-6 | 5-6 |
| | Appearance of Coated Layer | Good | Good |
| | Presence or absence of Interference fringe | Nothing | Nothing |
| | Presence or absence of Hays | Nothing | Nothing |
| | Hardness (Pencil Hardness) | 2H | 3H |
| | Anti-scratch Property (No. 0000, 1 kg Load, 10 Reciprocations) | No Scratch | No Scratch |
| | Adhesiveness (Cross-cut Test) | 100/100 | 100/100 |
| | Curling Property (mm) | 0-5 | 0-5 |
| | Water Contact Angle (°) | 84.0 | 61.2 |
| | Oleic Acid Contact Angle (°) | 24.7 | 22 |
| | Wiping-off Test (Finger print off test) | Excellent | Poor |
| | Antifouling Property (Adhesiveness of Oil Resistant Ink) | Poor | Poor |

As clearly showed in Table 3, the coating material which was obtained from the composition containing chemically modified colloidal silica applying the present invention exhibited excellent water repellency and excellent lipophilicity in comparison to the coating material not containing such colloidal silica. Other functions were almost not damaged. Further, excellent wiping out property and anti-fouling property were observed.

Example 19

Diene easily reacts with dienophile such as acrylate and mathacrylate by Diels-Alder reaction. As seen in the following chemical reaction equation, diene having an allylsilyl group was synthesized.

(19.1) To triphenylphosphine dibromide ($Ph_3PBr_2$; 468 mg, 1.108 mmol), distilled methylene chloride (5 mL) was added under a nitrogen atmosphere and dissolved. Then, diallyl (t-butyl)methoxy silane (55) (200 mg, 1.008 mmol) was added thereto and stirred at room temperature for 6 hours. After stirring, the intermediates (56) obtained was allowed to concentrate without purification, distilled tetrahydrofuran (5 ml) was added and cooled down to −78° C. 4-methoxy-3-butene-2-one (57) (0.14 ml, 0.916 mmol) was added thereto and stirring was continued for 15 minutes. Then 2.21 ml (1.1088 mmol) toluene solution of 0.5M hexamethyldisilazane potassium (potassium bis(trimethylsilyl)amide: KN(TMS)$_2$) was dropped and further stirred for 1 hour. Then the reacted mixture was kept at 0° C. and stirred for 4 hours. Then, it was quenched with saturated ammonium chloride aqueous solution, and the reaction mixture was warmed up to room temperature, then the obtained organic layer was separated. The obtained water layer was extracted with diethyl ether. The collected organic layer was washed with saturated saline solution, dried over anhydrous magnesium sulfate, then filtered, concentrated under reduced pressure, obtaining diene-containing allylsilane compound (57).

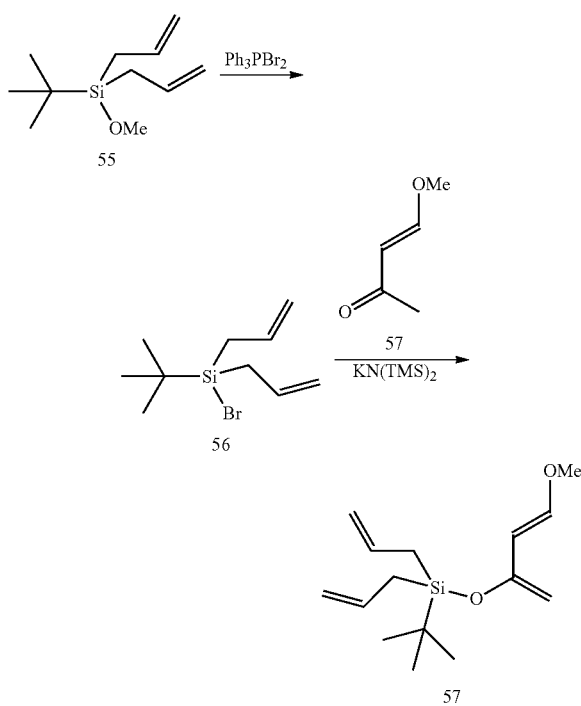

These physical and chemical analysis results according to ¹H NMR are shown below.

¹H NMR (CDCl₃) δ 1.021 (s, 9H), 1.698-1.869 (m, 4H), 3.646 (s, 3H), 4.142 (d, J=10.8 Hz, 2H), 4.863-5.002 (m, 4H), 5.336 (d, J=12.8 Hz, 1H), 5.953-5832 (m, 2H), 6.942 (d, J=12.4 Hz, 1H).

These physical and chemical analysis results support the chemical formula (57). The thus obtained diene-containing allylsilane compound represented by the chemical formula (57) reacts with a dienophile, generating various Diels-Alder adducts, which have an allylsilyl group, so that they act as silane coupling agents. They are further silane-coupling on the silane coupled base material via a surface hydroxyl group, being able to form a new silylether bond.

Example 20

(20.1) Under a nitrogen atmosphere, to 4-{3-(triallylsilyl) propyl}phenyl bromide (3) (4.76 g, 13.624 mmol), distilled tetrahydrofuran (20 ml) was added and cooled down to −5° C. Then 2.25 mL (4.5 mmol) diethyl ether solution of 2M isopropyl magnesium chloride (ⁱPrMgCl) and 5.39 mL (9 mmol) n-hexane solution of 1.67M n-butyl lithium (ⁿBuLi) were dropped. The mixture was heated to room temperature and stirred for 17 hours. After that, the mixture was cooled down to 0° C., then trichloro(phenyl)silane (PhSiCl₃ (2.18 ml, 13.624 mmol) was dropped, stirred at room temperature for 15 hours, to obtain dichlorosilyl body (59). Then, the mixture was cooled down to −5° C. Triethylamine (NEt₃) (5.70 ml, 40.87 mmol) and methanol (MeOH) (1.65 ml, 40.87 mmol) were added. The mixture was heated to room temperature and stirred for 3 hours. Then the mixture was cooled down to 0° C. and quenched with water. Then saturated ammonium chloride aqueous solution was added until the salt was completely dissolved. The obtained organic layer was separated and the obtained water layer was extracted with diethyl ether. The collected organic layer was washed each with saturated sodium bicarbonate aqueous solution and saturated saline solution in this order, dried over anhydrous magnesium sulfate. The mixture was filtered, and concentrated under reduced pressure, obtaining dimethoxysilyl body (60), a product (yield: 5.53 g, yield (%): 93%). These physical and chemical analysis results according to ¹H NMR are shown below.

¹H NMR (CDCl₃) δ 0.612-0.653 (m, 2H), 1.571 (d, J=8.4 Hz, 6H), 1.604-1.698 (m, 2H), 2.616 (t, J=7.6 Hz, 2H), 3.619 (s, 6H), 4.817-4.879 (m, 6H), 5.693-5.811 (m, 3H), 7.184 (d, J=8 Hz, 2H), 7.347-7.416 (m, 3H), 7.574 (d, J=6.8 Hz, 2H), 7.655 (d, J=6.4 Hz, 2H)

These physical and chemical analysis results support the chemical formula (60).

(20.1) Under a nitrogen atmosphere, to dimethoxysilyl body (60) (3.38 g, 7.74 mmol), distilled diethyl ether was added, then cooled to −78° C. 7.54 mL n-pentane solution of 1.54M ᵗBuLi (11.61 mmol) was added dropwise and stirred as it was for 17 hours. Then, the mixture was cooled to 0° C., quenched with water, then saturated ammonium chloride aqueous solution was added. The obtained organic layer was separated and then the obtained water layer was extracted with diethyl ether. The collected organic layer was washed with each saturated sodium bicarbonate aqueous solution and saturated saline solution in this order then dried over anhydrous magnesium sulfate. The mixture was filtered, concentrated under reduced pressure, obtaining t-butylsilyl body (61) (yield: 3.41 g, yield (%): 95%). These physical and chemical analysis results according to ¹H NMR are shown below.

¹H NMR (CDCl₃) δ 0.632-0.675 (m, 2H), 1.033 (s, 9H), 1.582 (d, J=7.6 Hz, 6H), 1.628-1.708 (m, 2H), 2.633 (t, J=7.8 Hz, 2H), 3.527 (s, 3H), 4.833-4.886 (m, 6H), 5.707-5.816 (m, 3H), 7.197 (d, J=7.2 Hz, 2H), 7.374-7.429 (m, 3H), 7.603 (d, J=8 Hz, 2H), 7.685 (d, J=7.2 Hz, 2H).

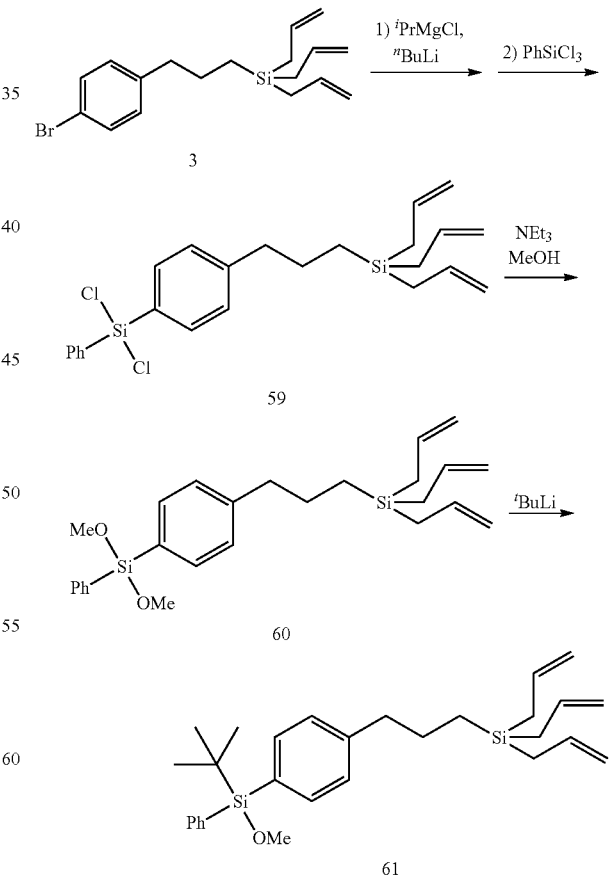

In Examples, specific (meth)allylsilane compounds, silane coupling agents using the same, functional materials prepared from the silane coupling agents were shown. When the substrates which are used as raw materials are changed, corresponding to those substances can be prepared. After the reaction between tri(meth)allylsilyl group-containing tertiary alcohol and triphosgene, an amino-acid derivative may be reacted to synthesize a (meth)allylsilane compound, then a functional material can be prepared.

For example, organic metal compounds such as Grignard reagent represented by tri(meth)allylsilylalkylmagnesium halide, tri(meth)alkylsilylaralkylmagnesium halide, tri (meth)allylsilylalkylphenylmagnesium halide, etc. are reacted with alkyltrialkoxysilanes such as tetraalkoxysilanes, tert-butyltrialkoxysilanes, etc. then the alkoxy of remaining alkoxysilyl groups are substituted for a halogen atom by halogeno-substituted as necessary. Thus various (meth)allylsilane compounds which are included in the present invention can be prepared. Further, the halogen atom which is halogen-substituted may be reacted with various alcohols such as functional alcohols to introduce alkoxy groups. A bond which is originated from a silicon atom and an oxygen atom of protected functional alcohol is not cut. Thus, such compounds can induce the sol-gel reaction based on hydrolysis of allylsilyl groups.

Further, after a reaction of such organic metal compound and an aldehyde derivative and then halogenation is carried out so that it is induced to an organic metal compound such as a Grignard reagent. Next, reaction with hydroxy-containing phenyl trialkoxysilane derivative is carried out to introduce a polymerizable unsaturated group. Thus, (meth)allylsilane compound which is included in the present invention may be prepared. Further, remaining alkoxysilyl group is introduced to a halogenosilyl group and then another (meth)allylsilane compound of the present invention may be prepared. If necessary, such organic metal compounds are reacted with unsaturated group-containing phenyltrialkoxysilane derivatives, thereby (meth)allylsilane compound of the present invention may be prepared. Further, the remaining alkoxysilyl group is introduced to a halogenosilyl group, thereby another (meth) allylsilane compound may be prepared.

These (meth)allylsilane compounds are reacted with polyols or sugars such as cyclodextrin, thereby a silane coupling agent of the present invention may be prepared.

From heterocyclic rings such as halogeno carbazole, etc., (meth)allylsilane compounds can be prepared in the same manner. Further, by repeating such preparation, conjugated system can be expanded and can be applied to various optical and electronic materials.

The silane coupling agents using such these compounds can be applied for functional materials by letting the coupling agents to be on the surface of various base materials such as silica gels, glasses, etc. through chemical reactions on the surfaces of various materials.

INDUSTRIAL APPLICABILITY

The (meth)allylsilane compounds and the silane coupling agents having the same of the present invention exhibit functionalities such as for example optical properties such as an anti-fogging property, an anti-reflective property, etc., a separation property in column chromatography, a charge transport property for electronic materials, catalytic property for chemical reactions, etc. to base materials. Therefore, the (meth)allylsilane compounds and the silane coupling agents having the same of the present invention are useful for raw materials to prepare functional materials.

These functional materials are used: as anti-fogging materials or anti-reflecting materials for glass windows, glasses and displays etc. in which cloudiness or fogging should be avoided and livingwares, electric appliances and electronic gadgets in which light reflection should be prevented; for a precise and sure separation as carrier of column chromatography for analysis or isolation in the art of fine chemicals or biochemicals; for electronic materials such as charge transport materials in electrophotographic photoreceptor, and hole transport materials of organic electroluminescence devices etc.; for catalysts for organic synthesis which is recovered and used repeatedly, in particular as an asymmetric catalyst used in various reactions such as redox reactions, asymmetric, nucleophilic substitution reactions, electrophilic substitution reactions, etc.

According to a process for manufacturing a functional material, this functional material can be manufactured simply, in high quality and in high yield, being useful in industrial production.

The coating materials formed from coating compositions containing (meth)allylsilane compound, specifically, the perfluoro group-containing (meth)allylsilane compounds of the present invention have an excellent anti-scratching property, moderate water and oil repellency which are required in electric appliances, housing for daily necessities, exterior of vehicles, building materials, etc.

What is claimed is:

1. A functional material, comprising:
   a base material comprising an exposed surface hydroxyl group; and
   a silane coupling agent ether-bonded to the base material by silane-coupling via the surface hydroxy group, the silane couple agent comprising a (meth)allylsilane compound,
   wherein:
      the (meth)allylsilane compound comprises a first functional group selected from:
         a substituted or unsubstituted (meth)allylsilyl group; and
         a halogenosilyl group bonded to a substituted or unsubstituted (meth)allylsilyl group via a first spacer group, the first spacer group comprising at least one of an alkylene group, an arylene group, an aralkylene group and a silyl group;
      the first functional group is bonded to a second functional group directly or through a second spacer group, the second spacer group comprising at least one of an alkylene group, an arylene group, an aralkylene group, a silyl group, an ox group, an alkylene ether group, and a poly(alkyleneoxy) group; and
      the second functional group is selected from the group consisting of:
         an amino group of an amino group-containing compound or an amide group derived from the amino group;
         a carbaminic acid ester group;
         an aromatic compound selected from a biphenyl compound, a triallylamine compound, and a carbazole compound;
         a polymerizable unsaturated group;
         a perfluoro group selected from the group consisting of a perfluoro alkyl group, a perfluoroalkenyl group, and a perfluoroaralkyl group;
         a hydroxyl group of a saccharide or a carbohydrate polyol, excluding when the second spacer group is an alkylene group, or an alkylene group and an arylene group;

a halogenosilyl group; and
a substituted silyl group in which a halogen atom of the halogenosilyl group is substituted with an alkyl group, an aryl group, a hydroxyl group, an alkoxy group, an aryloxy group, a mercapto group, an alkylthio group, an arylthio group, an amino group, a hydroxyl group of a sugar, a hydroxyl group of a hydrocarbon-based polyol, an amino group of an amino acid, a phosphoryl group, a silyl group, or a silyloxy group.

2. The functional material according to claim 1, further comprising a second silane coupling agent ether-bonded to the base material via the surface hydroxyl group through silane coupling, the second silane coupling agent comprising:
at least one of an alkyl group, a fluoroalkyl group having hydrogen atoms, a perfluoroalkyl group, and an aryl group, each of which is independently substituted or unsubstituted, and
a trialkoxysilyl group, a dialkoxy allyl silyl group, an alkoxy diallyl silyl group, or a triallyl silyl group.

3. The functional material according to claim 1, wherein the second functional group in the (meth)allylsilane compound is exposed on the base material.

4. The functional material according to claim 1, wherein the base material is a glass base material, a metal base material, a ceramics base material, a resin base material, or a surface coating base material made of any one of the base materials, each of which are treated with the silane coupling agent.

5. The functional material according to claim 1, wherein the functional material is an anti-fogging material, an optical material, a column chromatography carrier, a catalyst, or an electronic material, each of which are prepared by surface modification treated with the silane coupling agent.

6. The functional material according to claim 5, wherein the base material is a glass particle, a silica gel particle, an alumina particle, a metal particle, a ceramic particle, a resin particle or the particles having a chemically modified surface made of any one of the base materials, and the functional material is a column chromatography carrier.

7. The functional material according to claim 5, wherein the base material is a glass base material, a metal base material, a ceramics base material, a resin base material or a surface-coated base material made of any one of the base materials, and the functional material is the catalyst exhibiting a catalyzing function induced from the silane coupling agent.

8. The functional material according to claim 5, wherein the base material is a glass base material, a metal base material, a ceramics base material, a resin base material of surface modified base material made of any one of the base materials, and the functional material is the electronic material surface-treated with the silane coupling agent.

9. The functional material according to claim 1, wherein the ether bond is formed by the silane coupling of the silane coupling agent through a sol-gel method.

10. The functional material according to claim 1, wherein the ether bond is formed in anhydrous organic solvent by the silane coupling of the silane coupling agent.

11. The functional material according to claim 1, wherein the ether bond is formed by the silane coupling of the silane coupling agent at least in the presence of a hydrochloric acid, a sulfuric acid, a tetraalkoxysilane, a polycarboxylic acid halide, and a polycarboxylic acid anhydride.

12. The functional material according to claim 1, wherein the (meth)allylsilyl group in the (meth)allylsilane compound is a mono-, di-, or tri-(meth)allylsilyl group.

13. The functional material according to claim 1, wherein the (meth)allylsilyl group in the (meth)allylsilane compound is selected from the group consisting of an alkyl[di(meth)allyl]silyl group and a dialkyl[(meth)allyl]silyl group each of which has at least one of a linear, branched, or cyclic carbon chain having a carbon number of 1 to 24, and a tri(meth)allylsilyl group.

14. The functional material according to claim 1, wherein in the (meth)allylsilane compound, the silyl of at least one of the (meth)allylsilyl group, the silyl group, the halogenosilyl group, and the substituted silyl group is mono- or di-substituted with a linear, branched, and/or cyclic alkyl group having a carbon number of 1 to 24.

15. The functional material according to claim 1, wherein in the (meth)allylsilane compound, the amino group-containing compound is a primary amine, a secondary amine, or an amino acid.

16. The functional material according to claim 1, wherein in the (meth)allylsilane compound, the halogenosilyl group is a fluoro-, chloro-, bromo-, or iodo-silyl group.

17. The functional material according to claim 1, wherein in the (meth)allylsilane compound, the polymerizable unsaturated group is an acrylic group, a methacrylic group, a styril group, or a terminally unsaturated alkenyl group.

18. The functional material according to claim 1, wherein in the (meth)allylsilane compound, the perfluoro group comprises a linear, branched, or cyclic carbon chain having a carbon number of 1 to 24.

19. The functional material according to claim 1, wherein in the (meth)allylsilane compound, the perfluoro group is selected from the group consisting of:
a perfluoroalkenyl group having a carbon number of 1 to 24;
a perfluorocycloalkyl group having a carbon number of 3 to 24;
a perfluoroalkenyl group having a carbon number of 2 to 24;
a perfluorocycloalkenyl group having a carbon number 3 to 24;
a perfluoroaralkyl group having a carbon number of 7 to 24.

20. The functional material according to claim 1, wherein in the (meth)allylsilane compound, the perfluoro group is a perfluoroalkenyl group represented by n-$C_6F_{13}$— group or represented by the following chemical formula (I):

21. The functional material according to claim 1, wherein in the (meth)allylsilane compound, in the second spacer group, the alkylene group, the arylene group, the aralkylene group, and the alkylene ether group are each independently a linear and/or a branched chain having a carbon number of 1 to 36, and the poly(alkyleneoxy) group has a molecular weight of 88 to 50,000.

22. The functional material according to claim 1, wherein in the (meth)allylsilane compound, at least one of a hydroxyl group, a (meth)acryloyl group, and a (meth)acryloyloxy group is bonded to the second spacer group.

23. The functional material according to claim 1, wherein in the (meth)allylsilane compound, a (meta)silyl is carbon-increased to an allyl of the (meth)allylsilyl.

24. The functional material according to claim 1, wherein in the (meth)allylsilane compound, the (meth)allylsilyl group is a dendrimer-like structure.

25. The functional material according to claim 1, wherein in the (meth)allylsilane compound, the (meth)allylsilyl group is formed by bonding an unsubstituted alkyl group to a silane group.

26. The functional material according to claim 1, wherein the (meth)allylsilane compound having a perfluoro group is manufactured via a method for manufacturing comprising:
reacting any one of
a perfluoroalkyl-1,2-epoxypropane having a linear, branched and/or cyclic perfluoroalkyl having a carbon number of 1 to 24,
a hexafluoropropene trimer, and
a hexafluoropropene trimer having a fluoro carbon of the fluoroethylene group substituted with a glycidol or a glycerin diglycidylether,
with a substituted or unsubstituted organic metal compound selected from the group consisting of:
a tri-(meth)allylsilyl alkylene metal compound having a linear, branched and/or cyclic alkylene of having a carbon number 1 to 36,
an alkyl[di(meth)allyl]silyl alkylene metal compound, and
a dialkyl[(meth)allyl]silyl alkylene metal compound having a linear, branched and/or cyclic alkyl having a carbon number 1 to 24 and a linear, branched and/or cyclic alkylene having a carbon number 1 to 36,
to obtain the (meth)allylsilane compound having the perfluoro group.

27. The functional material according to claim 26, wherein in the method for manufacturing the (meth)allylsilane compound having the perfluoro group, a hydroxyl group generated between the substituted or unsubstituted organic metal compound and the perfluoroalkyl-1,2-epoxypropane is esterified with a (meth)acrylic ester group.

28. The functional material according to claim 1, wherein in the silane coupling agent, the (meth)allylsilane compound has a functional group selected from the group consisting of a catalytic functional group, a conjugated functional group, and a molecular recognition functional group.

29. The functional material according to claim 28, wherein in the silane coupling agent,
the catalytic functional group is a phosphine-containing functional group and/or a heterocycle-containing functional group;
the conjugated functional group is a carbazole ring-containing functional group, a polyene-containing functional group, a polyyne-containing functional group, and/or a polyarene-containing functional group; and
the molecular recognition functional group is an optically active site-containing functional group.

30. The functional material according to claim 1, wherein the silane coupling agent is manufactured from a (meth)allylsilyl group and a halogenosilyl group bonded to the (meth)allylsilyl group via a first spacer group containing an alkyl group, an aryl group, an aralkyl group and/or silyl group, or from a (meth)allylsilane compound having a (meth)allylsilyl group and a halogenosilyl group bonded to the (meth)allylsilyl group via a second spacer group containing an alkyl group, an aryl group, an aralkyl group and/or oxy group, by a method comprising:
substituting a halogen of the halogenosilyl group with an alkyl group, an aryl group, a hydroxyl group, an alkoxy group, an allyloxy group, a mercapto group, an alkylthio group, an arylthio group, an amino group, a hydroxyl group of a sugar, a hydroxyl group of a hydrocarbon-based polyol, an amino group of an amino acid, a phosphoryl group, a silyl group, or a silyloxy group.

31. A method for manufacturing a functional material comprising a silane couple agent and a base material containing an exposed surface hydroxyl group, the method comprising:
ether-bonding the silane coupling agent to the base material by silane coupling via the surface hydroxyl group, wherein:
the silane couple agent comprises a (meth)allylsilane compound;
the (meth)allylsilane compound comprises a first functional group selected from:
a substituted or unsubstituted (meth)allylsilyl group; and
a halogenosilyl group bonded to a substituted or unsubstituted (meth)allylsilyl group via a first spacer group, the first spacer group comprising at least one of an alkylene group, an arylene group, an aralkylene group and a silyl group;
the first functional group is bonded to a second functional group directly or through a second spacer group, the second spacer group comprising at least one of an alkylene group, an arylene group, an aralkylene group, a silyl group, an oxy group, an alkylene ether group, and a poly(alkyleneoxy) group; and
the second functional group is selected from the group consisting of:
an amino group of an amino group-containing compound or an amide group derived from the amino group;
a carbaminic acid ester group;
an aromatic compound selected from a biphenyl compound, a triallylamine compound, and a carbazole compound;
a polymerizable unsaturated group;
a perfluoro group selected from the group consisting of a perfluoro alkyl group, a perfluoroalkenyl group, and a perfluoroaralkyl group;
a hydroxyl group of a saccharide or a carbohydrate polyol, excluding when the second spacer group is an alkylene group, or an alkylene group and an arylene group;
a halogenosilyl group; and
a substituted silyl group in which a halogen of the halogenosilyl group is substituted with an alkyl group, an aryl group, a hydroxyl group, an alkoxy group, an aryloxy group, a mercapto group, an alkylthio group, an arylthio group, an amino group, a hydroxyl group of a sugar, a hydroxyl group of a hydrocarbon-based polyol, an amino group of an amino acid, a phosphoryl group, a silyl group, or a silyloxy group.

32. The method for manufacturing the functional material according to claim 31, wherein the ether-bonding is formed by the silane coupling reaction of the silane coupling agent through a sol-gel method.

33. The method for manufacturing the functional material according to claim 31, wherein another silane coupling agent having an alkyl group, a fluoroalkyl group having hydrogen atoms, a perfluoroalkyl group and/or an aryl group, each of which is substituted or unsubstituted, and has a trialkoxysilyl group, a dialkoxy allyl silyl group, an alkoxy diallyl silyl group, or a triallyl silyl group, is further ether-bonded on the base material via the surface hydroxyl group through silane coupling reaction.

34. The method for manufacturing the functional material according to claim 31, wherein after the silane coupling reaction, a trihalogenosilane is reacted with a terminal unsaturated carbon of the (meth)allylsilyl group derived from the silane coupling agent, introducing a trihalogenosilyl group; and a (meth)allylsilyl group-containing organic metal compound is reacted with the halogeno group, amplifying the (meth)allylsilyl group-containing group.

35. The method for manufacturing the functional material according to claim 31, wherein the silane coupling is carried out in a process in which the silane coupling agent is treated with an acid aqueous solution.

36. The method for manufacturing the functional material according to claim 35, wherein after the silane coupling agent is treated with the acid aqueous solution, a process in which the silane coupling agent is reacted with tetraalkoxysilane and the reaction is performed in the presence of a concentrated sulfuric acid are carried out, the silane coupling is carried out.

37. The method for manufacturing the functional material according to claim 31, wherein the silane coupling reaction is carried out in a process in which the silane coupling agent is reacted with a polycarboxylic acid halide or polycarboxylic acid anhydride.

38. The method for manufacturing the functional material according to claim 31, wherein a process to treat with a polycarboxylic acid halide or a polycarboxylic anhydride is performed in an anhydrous organic solvent.

39. A coating composition comprising the functional material according to claim 1.

40. The coating composition according to claim 39, wherein the coating composition contains filler particles comprised of the base material of the functional material.

41. A coating material, wherein the coating composition according to claim 39 is coated on a substrate and cured by heating or irradiation with an active energy ray.

42. The functional material according to claim 1, wherein the second functional group is an amino group of an amino acid.

* * * * *